US007598079B2

(12) United States Patent
Kastelic et al.

(10) Patent No.: US 7,598,079 B2
(45) Date of Patent: Oct. 6, 2009

(54) ASSAY FOR IDENTIFYING COMPOUNDS WHICH AFFECT STABILITY OF MRNA

(75) Inventors: Tania Kastelic, Coquitlam (CA); Dominique Cheneval, Coquitlam (CA)

(73) Assignee: Novation Pharmaceuticals, Inc., New Westminster, British Columbia ( * ) Notice: Subject to any disclaimer, the term of this patent is extended or adjusted under 35 U.S.C. 154(b) by 384 days.

(21) Appl. No.: 10/814,634

(22) Filed: Apr. 1, 2004

(65) Prior Publication Data

US 2004/0231007 A1 Nov. 18, 2004

Related U.S. Application Data

(63) Continuation-in-part of application No. 09/869,159, filed as application No. PCT/CA99/01235 on Dec. 23, 1999, now abandoned.

(30) Foreign Application Priority Data

Dec. 24, 1998 (GB) ................................. 9828709.7

(51) Int. Cl.
*G01N 33/53* (2006.01)
*C12N 5/00* (2006.01)
(52) U.S. Cl. ........................... 435/325; 435/7.1; 435/29
(58) Field of Classification Search ....................... None
See application file for complete search history.

(56) References Cited

U.S. PATENT DOCUMENTS

| 5,444,149 | A | 8/1995 | Keene et al. |
| 5,587,300 | A | 12/1996 | Malter |
| 5,698,427 | A | 12/1997 | Keene et al. |
| 5,731,343 | A | 3/1998 | Feng et al. |
| 6,635,671 | B1 | 10/2003 | Kastelic et al. |
| 7,078,171 | B2 | 7/2006 | Giordano et al. |
| 2004/0214223 | A1 | 10/2004 | Cao et al. |
| 2005/0048549 | A1 | 3/2005 | Cao et al. |
| 2007/0190532 | A1 | 8/2007 | Katelic et al. |

FOREIGN PATENT DOCUMENTS

| GB | 9828707.1 | 2/1999 |
| GB | 9828710.5 | 2/1999 |
| WO | WO-93/20212 A1 | 10/1993 |
| WO | WO-95/33831 A1 | 12/1995 |
| WO | WO-98/39484 A1 | 9/1998 |
| WO | WO-99/61605 A2 | 12/1999 |
| WO | WO-99/61605 A3 | 12/1999 |
| WO | WO-99/61605 C1 | 12/1999 |
| WO | WO-00/38674 A1 | 7/2000 |
| WO | WO-00/39314 A1 | 7/2000 |
| WO | WO-02/072844 A1 | 9/2002 |
| WO | WO-2004/065561 A2 | 8/2004 |

OTHER PUBLICATIONS

Lemm and Ross (Molecular and Cellular Biology, 2002, vol. 22, No. 12, pp. 3959-3969).*
Banholzer et al (Molecular Cellular Biology, 1997, vol. 17, No. 6, pp. 3254-3260).*
Zubiaga et al. (1995, MCB, vol. 15, No. 4, pp. 2219-2230).*
Kastelic et al (Cytokine, 1996. vol. 8, No. 10, pp. 751-761).*
Levy et al (JBC, 1996, vol. 271, No. 5, pp. 2746-2753).*
Rajagopalan et al (Journal of Neurochem. 2000. vol. 74, pp. 52-59).*
Capaccioli et al. (Oncogene, 1996, vol. 13, pp. 106-115).*
Yeilding et al (Molecular and Cellular Biology, 1996.vol. 16, No. 7, pp. 3511-3522).*
Zhang et al (Biochemical and Biophysical Research Communications, 1996. vol. 227, No. 3, pp. 707-711).*
Merriam Webster Online dictionary definition of "derive.", (2007).*
Akashi, M. et al. (1994). "Number and Location of AUUUA Motifs: Role in Regulating Transiently Expressed RNAs," *Blood* 83:3182-3187.
Auwerx, J. (1991). "The Human Leukemia Cell Line, THP-1: A Multifaceted Model for the Study of Monocyte-Macrophage Differentiation," *Experienta* 47:22-31.
Banholzer, R. et al. (Jun. 1997). "Rapamycin Destabilizes Interleukin-3 mRNA in Autocrine Tumor Cells by a Mechanism Requiring an Intact 3' Untranslated Region," *Molecular and Cellular Biology* 17(6):3254-3260.
Bernstein, P.L. et al. (Apr. 1992). "Control of c-*myc* mRNA Half-Life in vitro by a Protein Capable of Binding to a Coding Region Stability Determinant," *Genes Dev.* 6(4):642-654.
Beutler, B. et al. (1988). "Assay of a Ribonuclease That Preferentially Hydrolyses mRNAs Containing Cytokine-Derived UA-Rich Instability Sequences," *Biochem. Biophys. Res. Comm.* 152:973-980.
Chen, C.-Y.A. et al. (1994). "Interplay of Two Functionally and Structurally Distinct Domains of the c-*fos* AU-Rich Element Specifies Its mRNA-Destabilizing Function," *Mol. Cell. Biol.* 14:416-426.
Chen, C.-Y.A. et al. (1994). "Selective Degradation of Early-REsponse-Gene mRNAs: Functional Analyses of Sequence Features of the AU-Rich Elements," *Mol. Cell. Biol.* 14:8471-8482.
Chen, C.-Y.A. et al. (1995). "AU-Rich Elements: Characterizatiopn and Importance in mRNA Degradation," *TIBS* 20:465-470.
Chen, C.-Y.A. et al. (1995). "mRNA Decay Mediated by Two Distinct AU-Rich Elements from c-*fos* and Granulocyte-Macrophage Colony-Stimulating Factor Transcripts: Different Deadenylation Kinetics and Uncoupling from Translation," *Mol. Cell. Biol.* 15:5777-5788.
Claffey, K.P. et al. (Feb. 1998). "Identification of a Human VPF/VEGF 3' Untranslated Region Mediating Hypoxia-Induced mRNA Stability," *Mol. Biol. Cell* 9:469-481.
Cleveland, D.W. et al. (Nov. 1989). "Multiple Determinants of Eukaryotic mRNA Stability," *New. Biol.* 1(2):121-126.

(Continued)

*Primary Examiner*—Deborah Crouch
(74) *Attorney, Agent, or Firm*—Morrison & Foerster LLP

(57) ABSTRACT

The present invention relates to an assay for the identification of biologically active compounds, in particular to a reporter gene assay for the identification of compounds, which have an effect on mRNA stability. More particularly, the present invention relates to a reporter gene expression system and cell lines comprising said expression system. The invention further relates to compounds which destabilize mRNA.

21 Claims, 18 Drawing Sheets

OTHER PUBLICATIONS

Crawford, E.K. et al. (Aug. 1997). "The Role of 3' Poly(A) Tail Metabolism in Tumor Necrosis Factor-α Regulation," *J. Biol. Chem.* 272:21120-21127.

Danner, S. et al. (Feb. 1998). "Agonist REgulation of Human β₂-Adrenergic Receptor mRNA Stability Occurs via a Specific AU-Rich Element," *J. Biol. Chem.*273:3223-3229.

Fan, X.C. (Jun. 1998). "Overexpression of HuR, a Nuclear-Cytoplasmic Shuttling Protein, Increases the in vivo stability of ARE-Containing mRNAs," *EMBO J.* 17:3448-3460.

GenBank Accession No. AF022375, created Oct. 7, 1998, located at <http://www.ncbi.nlm.nih.gov/entrez/viewer.fcgi?db=nucleotide&val=3719220>, last visited on Feb. 7, 2007, two pages.

GenBank Accession No. D10493, created May 29, 2002, located at <http://www.ncbi.nlm.nih.gov/entrez/viewer.fcgi?db=nuccore&val=219932>, last visited on Feb. 7, 2007, seven pages.

GenBank Accession No. M13994, created Oct. 31, 1994, located at <http://www.ncbi.nlm.nih.gov/entrez/viewer.fcgi?db=nucleotide&val=179366>, last visited on Dec. 29, 2006, three pages.

GenBank Accession No. U40398, created Mar. 13, 1997, located at <http://www.ncbi.nlm.nih.gov/entrez/viewer.fcgi?db=nucleotide&val=1117909>, last visited on Dec. 29, 2006, three pages.

GenBank Accession No. X04500, created Nov. 14, 2006, located at <http://www.ncbi.nlm.nih.gov/entrez/viewer.fcgi?db=nucleotide&val=33788>, last visited on Dec. 29, 2006, six pages.

GenBank Accession No. Y00264, created Sep. 12, 1993, located at <http://www.ncbi.nlm.nih.gov/entrez/viewer.fcgi?db=nucleotide&val=28525>, last visited on Dec. 29, 2006, three pages.

Gil, P. et al. (1996). "Multiple Regions of the *Arabidopsis SAUR-AC1* Gene Control Transcript Abundance: the 3' Untranslated Region Functions as a mRNA Instability Determinant," *EMBO J.* 15:1678-1686.

Heaton, J.H. et al. (Jun. 1998). "Cyclic Nucleotide Regulation of Type-1 Plasminogen Activator-Inhibitor mRNA Stability in Rat Hepatoma Cells," *J. Biol. Chem.* 273:14261-14268.

International Search Report mailed Jun. 6, 2000, for PCT Application No. PCT/CA99/01235 filed Dec. 23, 1999, three pages.

Kastelic, T. et al. (Oct. 1996). "Induction of Rapid IL-1B mRNA Degradation in Thp-1 Cells Mediated Through the AU-rich Region in the 3' UTR by a Radcicol Analogue," *Cytokine* 8(10):751-761.

Klausner, R.D. et al. (1993). "Regulating the Fate of mRNA: The Control of Cellular Iron Metabolism," *Cell* 72:19-28.

Kobayashi, M. et al. (Jul. 1998). "Characterization of the 3' Untranslated Region of Mouse DNA Topoisomerase IIα mRNA," *Gene* 215:329-337.

Lagnado, C.A. et al. (1994). "AUUUA Is Not Sufficient to Promote Poly(A) Shortening and Degradation of an mRNA: The Functional Sequence Within AU-Rich Elements May Be UUAUUUA(U/A)(U/A)," *Mol. Cell. Biol.* 14:7984-7995.

Levy, A.P. et al. (1996). "Post-Transcriptional Regulation of Vascular Endothelial Growth Factor by Hypoxia," *J. Biol. Chem.* 271:2746-2753.

Levy, J.R. et al. (1995). "Sequence and Functional Characterization of the Terminal Exon of the Human Insulin Receptor Gene," *Biochim. Biophys. Acta* 1263:253-257.

Lewis, T. et al. (May 1998). "Mapping of a Minimal AU-Rich Sequence Required for Lipopolusaccharide-Induced Binding of a 55-kDa Protein on Tumor Necrosis Factor-α mRNA," *J. Biol. Chem.* 273:13781-13786.

Mitchell, P. et al. (Apr. 2000). "mRNA Stability in Eukaryotes," *Curr. Opin. Genet. Dev.* 10:193-198.

Mitchell, P. et al. (Jun. 2001). "mRNA Turnover," *Curr. Opin. Cell. Biol.* 13(3):320-325.

Nanbu, R. et al. (1994). "Multiple Instability-Regulating Sites in the 3' Untranslated Region of the Urokinase-Type Plasminogen Activator mRNA," *Mol. Cell. Biol.* 14:4920.

Ross, J. (Sep. 1995). "mRNA Stability in Mammalian Cells," *Microbiol. Rev.* 59(3):423- 450.

Sachs, A.B. (1993). "Messenger RNA Degradation in Eukaryotes," *Cell* 74:413-421.

Sambrook, J. et al. (1989). "Calcium Phosphate-Mediated Transfection of Adherent Cells in Suspension" *In* Chapter 16 *In Molecular Cloning A Laboratory Manual*, Cold Spring Harbor Labortory Press: Cold Spring Harbor, NY, p. 16.37.

Sambrook, J. et al. (1989). "Standard Protocol for Calcium Phosphate-Mediated Transfection of Adherent Cells" *In* Chapter 16 *In Molecular Cloning A Laboratory Manual*, Cold Spring Harbor Labortory Press: Cold Spring Harbor, NY, pp. 16.33-16.36.

Shaw, G. et al. (1986). "A Conserved AU Sequence from the 3' Untranslated Region of GM-CSF mRNA Mediates Selective mRNA Degradation," *Cell* 46:659-667.

Shyu, A.-B. et al. (1991). "Two Distinct Destabilizing Elements in the c-*fos* Message Trigger Deadenylation as a First Step in Rapid mRNA Decay," *Genes & Development* 15:221-231.

Staton, J.M. et al. (Aug. 2000). "Hormonal Regulation of mRNA Stability and RNA-Protein Interactions in the Pituitary," *J. Mol. Endocrinology* 25(1):17-34.

Stoecklin, G. et al. (1994). "Functional Hierarchy of AUUUA Motifs in Mediating Rapid Interleukin-3 mRNA Decay," *J. Biol. Chem.* 269:28591-28597.

Stolle, C.A. et al. (1988). "Cellular Factor Affecting the Stability of β-Globin mRNA," *Gene* 62:65-74.

Sullivan, M.L. et al. (1996). "Mutational Analysis of the DST Element in Tobacco Cells and Transgenic Plants: Identification of Residues Critical for mRNA Instability," *RNA* 2:308-315.

Wilusz, C.J. et al. (Apr. 11, 2001). "The Cap-To-Tail Guide to mRNA Turnover," *Nat. Rev. Mol. Cell. Biol.* 2(4):237-246.

Winstall, E. et al. (1995). "Rapid mRNA Degradation Mediated by the c-*fos* 3' AU-Rich Element and That Mediated by the Granulocyte-Macrophage Colony-Stimulating Factor 3' AU- Rich Element Occur Through Similar Polysome-Associated Mechanisms," *Mol. Cell. Biol.* 15:3796-3804.

Xu, N. et al. (Aug. 1997). "Modulation of the Fate of Cytoplasmic mRNA by AU-Rich Elements: Key Sequence Features Controlling mRNA Deadenylation and Decay," *Mol. Cell. Biol.* 18:4611-4621.

Zhang, G. et al. (Oct. 23, 1996). "An Enhanced Green Fluorescent Protein Allows Sensitive Detection of Gene Transfer in Mammalian Cells," *Biochemical and Biophysical Research Communications* 227(3):707-711.

Zhang, S. et al. (1995)."Indentification and Characterization of a Sequence Motif Involved in Nonsense-Mediated mRNA Decay," *Mol. Cell. Biol.* 15:2231-2244.

Zubiaga, A.M. et al. (Apr. 1995). "The Nonamer UUAUUUAUU Is the Key AU-Rich Sequence Motif That Mediates mRNA Degradation," *Molecular and Cellular Biology* 15(4):2219-2230.

Chrzanowska-Lightowlers, Z.M.A. et al. (2001). *RNA* 7(3):435-444.
Dalgleish, G. et al. (2001). *J. Biol. Chem.* 276(17):13593-13599.
Dean, J.L.E. et al. (2001). *Mol. Cell Biol.* 21(3):721-730.
Dean, J.L.E. et al. (2002). *Biochem J.* 366:709-716.
Dibbens, J.A. et al. (1999). *Mol. Biol. Cell* 10(4):907-919.
Herrick, D.J. et al. (1994). *Mol. Cell Biol.* 14:2119.
Laterza, O.F. et al. (2000). *Am J. Physiol. Renal. Physiol.* 278(6):F970-F977.
Lee, W.Y. et al. (2000). *J. Biol. Chem.* 275(43):33998-34008.
Ming, X-F. et al. (1998). *EMBO J.* 17(20):6039-6048.
Schiavone, N. et al. (2000). *FASEB J.* 14(1):174-184.
Shyu, A-B. et al. (1989). *Genes Dev.* 3:60-72.
Stoecklin, G. et al. (2000). *Mol. Cell. Biol.* 20(11):3753-3763.
Thames, E.L. et al. (2000). *Biochem. J.* 351(1):133-142.
Tian, D. et al. (1998). *J. Biol. Chem.* 273(38):24861-24866.
Winzen, R. et al. (1999). *EMBO J.* 18:4969-4980.
Yeilding, N.M. et al. (1997). *Mol. Cell. Biol.* 17(5):2698-2707.
Zhang, W. et al. (1993). *Mol. Cell. Biol.* 13:7652-7665.

* cited by examiner

Shown is the 3'UTR of the human IL1B sequence from accession number M15330.
* Represents the stop codon.

*AGAGAGCTGTACCCAGAGAGTCCTGTGCTGAATGTGGACTCAATCCCTAG
GGCTGGCAGAAAGGGAACAGAAAGGTTTTGAGTACGGCTATAGCCTGGAC
TTTCCTGTTGTCTACACCAATGCCCAACTGCCTGCCTTAGGGTAGTGCTAA
GAGGATCCCTGTCCATCAGCCAGGACAGTCAGCTCTCTCCTTTCAGGGCC
AATCCCCAGCCCTTTGTTGAGCCAGGCCTCTCCACCTCTCCTACTCACT
TAAAGCCCGCCTGACAGAAACCACGGCCCACATTTGGTTCTAAGAAACCTC
TGTCATTCGCTCCCACATTCTGATGAGCAACCGCTTCCCTA*ATTTATTTATT*
*TA*TTTGTTTGTTTATTCATTTAATCAAGGGGGCAAG
AAGTAGCAGTGTCTGTAAAGAGCCTAGTTTTAATCAGTCCTTAATTAAGACTG
TCAATTTGGACTGGTGTGCTCTCTTTAAATCAAGTCCTTAATTAAGACTG
AAATATAAGCTCAGATTA*TTTAAA*TGGGAATA*TTTATA*AATGAGCAAA
TATCATACTGTTCAATGGTTCTGAAATAAACTTCTCTGAAG

FIGURE 1

```
ATGGCTTCCCTATTTATTTATTTGTTTGTCCAACCT
||||||||||||||||||||||||||||||||||||
GGATACCGAAGGATAAATAAATAAACAAACAGGTT
```

FIGURE 2

APP construct:

■ AUUUA {Bold/Underline}
☆ potential polyA signal sequence {Bold/Italics}
Restriction Sites {Bold}

```
        NotI
   1  GCGGCCGCCA CAGCAGCCTC TGAAGTTGGA CAGCAAAACC ATTGCTTCAC TACCCATCGG TGTCCATTTA TAGAATAATG TGGGAAGAAA CAAACCCGTT
 101  TTATGATTTA CTCATTATCG CCTTTTGACA GCTGTGCTGT AACACAAGTA GATGCCTGAA CTTGAATTAA TCCACACATC AGTAATGTAT TCTATCTCTC
 201  TTTACATTTT GGTCTCTATA CTACATTATT AATGGGTTTT GTGTACTGTA AAGAATTAAG CTGTATCAAA CTAGTGCATG AATAGATTCT CTCCTGATTA
 301  TTTATCACAT AGCCCCTTAG CCAGTTGTAT ATTATTCTTG TGGTTTGTGA CCCAATTAAG TCCTACTTTA CATATGCTTT AAGAATCGAT GGGGATGCT
 401  TCATGTGAAC GTGGGAGTTC AGCTGCTTCT CTTGCCTAAG TATTCCTTTC CTGATCACTA TGCATTTTAA AGTTAAACAT TTTTAAGTAT TTCAGATGCT
 501  TTAGAGAGAT TTTTTTTTCC ATGACTGTAC AGATTGCTGC TTCTGCTATA TTTGTGATAT AGGAATTAAG AGGATACACA CGTTTGTTTC
 601  TTCGTGCCTG TTTTATGTGC ACACATTAGG CATTGAGACT TCAAGCTTTT CTTTTTTGT CCACGTATCT TTGGGTCTTT GATAAAGAAA AGAATCCCTG
 701  TTCATTGTAA GCACTTTAC GGGGCGGGTG GGGAGGGGTG CTCTGCTGGT CTTCAATTAC CAAGAATTCT CCAAAACAAT TTTCTGCAGG ATGATTGTAC
 801  AGAATCATTG CTTATGACAT GATCGCTTTC TACACTGTAT TACATAAATA AATTAAATAA AATAACCCCG GCAAGACTT TCTTTGAAG GATGACTACA
 901  GACATTAAAT AATCGAAGTA ATTTTGGGTG GGGAGAAGAG GCAGATTCAA TTTTCTTTAA CCAGTCTGAA GTTCATTTA TGATACAAAA GAAGATGAAA
1001  ATGGAAGTGG CAATATAAGG GGATGAGGAA GGCATGCCTG GACAAACCCT TCTTTAAGA TGTGTCTTCA ATTGTATAA AATGGTGTTT TCATGTAGCG
1101  GCCGC
       NotI
```

Length: 1105 bp

FIGURE 9 stop codon {Bold/Italics/Underline}

TNF-α construct:

■ AUUUA {Bold/Underline}
☆ Potential polyA signal sequence {Bold/Italics}
Restriction Sites {Bold}

```
      NotI
  1   GCGGCCGCTG AGGAGGACGA ACATCCAACC TTCCCAAACG CCTCCCCTGC CCCAATCCCT
 61   TTATTACCCC CTCCTTCAGA CACCCCTCAAC CTCTTCTGGC TCAAAAAGAG AATTGGGGGC
121   TTAGGGTCGG AACCCAAGCT TAGAACTTTA AGCAACAAGA CCACCACTTC GAAACCTGGG
181   ATTCAGGAAT GTGTGGCCTG CACAGTGAAG TGCTGGCAAC CACTAAGAAT TCAAACTGGG
241   GCCTCCAGAA CTCACTGGGG CCTACAGCTT TGATCCCTGA CATCTGGAAT CTGGAGACCA
301   GGGAGCCTTT GGTTCTGGCC AGAATGCTGC AGGACTTGAG AAGACCTCAC CTAGAAATTG
361   ACACAAGTGG ACCTTAGGCC TTCCTCTCTC CAGATGTTTC CAGACTTCCT TGAGACACGG
421   AGCCCAGCCC TCCCCATGGA GCCAGCTCCC TCTATTATTG TTTGCACTTG TGATTATTTA
481   TTATTTATT ATTATTATT TATTTACAGA TGAATGTATT TATTTGGGAG ACCGGGGTAT
541   CCTGGGGGAC CCAATGTAGG AGCTGCCTTG GCTCAGACAT GTTTTCCGTG AAAACGGAGC
601   TGAACAATAG GCTGTTCCCA TGTAGCCCCC TGGCCTCTGT GCCTTCTTTT GATTATGTTT
661   TTTAAAATAT TTATCTGATT AAGTTGTCTA AACAATGCTA ATTTGTGTGAC CAACTGTCAC
721   TCATTGCTGA GCCTCTGCTC CCCAGGGGAG TTGTGTCTGT AATCGCCCTA CTATTCAGTG
781   GCGAGAAATA AAGTTTGCTT CATATG
                                NdeI
```

Length: 806 bp

FIGURE 13

VEGF construct: ──■──■■──■──────■──■─★

■ AUUUA {Bold/Underline}
★ Potential polyA signal sequence {Bold/Italics}
  Restriction Sites {Bold}

```
       NotI
   1   GCGGCCGCAT TGCTGTGCTT TGGGGATTCC CTCCACATGC TGCACGCGCA TCTCGCCCCC AGGGGCACTG CCTGGAAGAT TCAGGAGCCT GGGCGGCCTT
 101   CGCTTACTCT CACCTGCTTC TGAGTTGCCC TCATCCTCTT CCTGCTCCCC AGGAGCCAC  TGGCAGATGT CCCGGCGAAG AGAAGAGACA CATTGTTGGA AGAAGCAGCC CATGACAGCT
 201   CCCCTTCCTG GGACTCGCCC TCATCCTCTT CCTGCTCCCC TTCCTGGGGT GCAGCCTAAA AGGACCTATG TCCTCACACC ATTGAAACCA CTAGTTCTGT
 301   CCCCCCAGGA GACCTGGTTG TGTGTGTGTG AGTGGTTGAC CTTCCTCCAT CCCCTGGTCC TTCCCCTTCC ACAGAGAGAC AGGGCAGGAT
 401   CCACGTGCCC ATTGTGGAGG CAGAGAAAAG TTTATATACGG TACTTATTTA ATATCCCTTT TTAATTAGAA ATTAAAACAG TTAATTTAAT
 501   TAAAGAGTAG GGTTTTTTTT CAGTATTCTT GGTTAATATT TAATTTCAAC TATTTATGAG ATGTATCTTT TGCTCTCTCT TTTGTACGG
 601   TTTTTGTATA TAAAATTCAT GTTTCCAATC TCTCTCTCCC TGATCGGTGA CAGTCACTAG CTTATCTTAT ACAGATATTT AATTTTGCTA ACACTCAGCT
 701   CTGCCCTCCC CGATCCCCTG GCTCCCCCAGC ACACATTCCT TTGAAATAAG GTTTCAATAT ACATCTACAT ACTATATATA TATATTTGGC AACTTGTATT
 801   TGTGTGTATA TATATATATA TATGTTTATG TATATATGTG ATTCTGATAA AATAGACATT GCTATTCTGT TTTTTATATG TAAAAACAAA ACAAGAAAAA
 901   ATAGAGAATT CTACACACTA AATCTCTCTC CTTTTTTAAT TTTAATATTT GTTATCATTT ATTTATTGGT GCTACTGTTT ATCCGTAATA ATTGTGGGGA
1001   AAAGATATTA ACATCACGTC TTTGTCTCTA GTGCAGTTTT TCGAGATATT CCGTAGTACA TATTTATTTT TAAACAACGA CAAAGAAATA CAGAACATAT
1101   G
                                                                                                                      NdeI
```

Length: 1101 bp

FIGURE 15

VEGF 3'UTR hypoxia domain construct:

AUUUA {Bold/Underline}
■ Restriction Sites {Bold}

```
     NotI
  1  GCGGCCGCAT TCCTGTAGAC ACACCCACCC ACATACATAC ATTTATATAT
 51  ATATATATTA TATATATATA AAATAAATA  TCTCTATTTT ATATATATAA
101  AATATATATA TTCTTTTTTT AAATTAACAG TGCTAATGTT ATTGGTGTCT
151  TCACTGGATG AACATATG
                     NdeI
```

Length: 168 bp

ASSAY FOR IDENTIFYING COMPOUNDS WHICH AFFECT STABILITY OF MRNA

CROSS REFERENCE TO RELATED APPLICATION

This application is a Continuation-In-Part of U.S. application Ser. No. 09/869,159 filed Dec. 23, 1999, the entire disclosure of which is incorporated herein by reference.

FIELD OF INVENTION

The present invention relates to the field of biological assays and in particular to an assay for the identification of biologically active compounds which have an effect on mRNA stability.

BACKGROUND OF THE INVENTION

Messenger RNA expression in mammalian cells is highly regulated. Traditionally, emphasis has been placed on elucidating mechanisms by which genes are regulated at the transcriptional level; however, steady-state levels of mRNA is also dependent on its half-life or degradation rate. Changes in mRNA stability play an important role in modulating the level of expression of many eukaryotic genes and different mechanisms have been proposed for the regulation of mRNA turnover (Cleveland and Yen, 1989, New Biol. 1:121; Mitchell and Tollervey, 2000, Curr. Opin. Genet. Dev. 10:193; Mitchell and Tollervey, 2001, Curr. Opin. Cell. Biol. 13:320; Ross, J. 1995, Microbiol. Rev. 59:423; Sachs, A. B., 1993, Cell 74:413; Staton et al. 2000, J. Mol. Endocrinology 25:17; Wilusz et al. 2001, Nat. Rev. Mol. Cell Biol. 2:237). However, the regulation of mRNA stability is complex. Regulation can involve sequence elements in the mRNA itself, activation of nucleases, as well as the involvement of complex signal transduction pathway(s) that ultimately influence trans-acting factors' interaction with mRNA stability sequence determinants.

Recently, it has become increasingly apparent that the regulation of RNA half-life plays a critical role in the tight control of gene expression and that mRNA degradation is a highly controlled process. RNA instability allows for rapid up- or down-regulation of mRNA transcript levels upon changes in transcription rates. A number of critical cellular factors, e.g. transcription factors such as c-myc, or gene products which are involved in the host immune response such as cytokines, are required to be present only transiently to perform their normal functions. Transient stabilisation of the mRNAs which code for these factors permits accumulation and translation of these messages to express the desired cellular factors when required; whereas, under nonstabilised, normal conditions the rapid turnover rates of these mRNAs effectively limit and "switch off" expression of the cellular factors. Thus, aberrant mRNA turnover usually leads to altered protein levels, which can dramatically modify cellular properties.

The stabilization of mRNA appears to be a major regulatory mechanism involved in the expression of inflammatory cytokines, growth factors, and certain proto-oncogenes. In the diseased state, mRNA half-life and levels of disease-related factors are significantly increased due to mRNA stabilization (Ross, J. 1995, Microbiol. Rev. 59:423; Sachs, A. B., 1993, Cell 74:413; Staton et al. 2000, J. Mol. Endocrinology 25:17; Wilusz et al. 2001, Nat. Rev. Mol. Cell Biol. 2:237). Transcription rates and mRNA stability are often tightly and coordinately regulated for transiently expressed genes such as c-myc and c-fos, and cytokines such as IL-1, IL-2, IL-3, TNFα, and GM-CSF. In addition, abnormal regulation of mRNA stabilisation can lead to unwanted build up of cellular factors leading to undesirable cell transformation, e.g. tumour formation, or inappropriate and tissue damaging inflammatory responses.

Although the mechanisms which control mRNA stability are far from understood, sequence regions have been identified in a number of mRNAs, which appear to confer instability on the mRNAs which contain them. These sequence regions are referred to herein as "mRNA instability sequences". For example, typical mRNA instability sequences are the AREs (adenylate/uridylate (AU) rich elements), which are found in the 3' UTR (3' untranslated region) of certain genes including a number of immediate early genes and genes coding for inflammatory cytokines, e.g. IL-1β and TNFα. The best characterized AU-rich element is the so-called Shaw-Kamen box or AUUUA motif (Shaw and Kamen, 1986, Cell 46:659). Multiple AUUUA sequences (in close proximity or in tandem) or AU-rich regions have been implicated in mRNA instability. For example, mRNA instability sequences described in the literature references identified below contain one or more copies of sequence motifs, e.g. selected from: AUUUA; UAUUUAU; UUAUUUA(U/A)(U/A), and AUUUAUUUA. Typically, in order to function as an instability determinant, the AUUUA motifs should be arranged in tandem, forming at least one UUAUUUAU/AU/A element (Lagnado et al., 1994, Mol. Cell. Biol. 14:7984).

The following publications include extensive discussion of mRNA instability sequences and AREs, the sequences motifs, which they contain and (minimum) sequence requirements for mRNA destabilisation, as well as identifying a number of mRNA instability sequences and the genes which contain them:

Shaw and Kamen, Cell, 1986, 46:659-667 (GM-CSF);
Shyu et al., Genes & Development, 1991, 15:221-231 (c-fos);
Sachs, Cell, 1993, 74:413-421 (Review. "Messenger RNA Degradation in Eukaryotes");
Chen et al., Mol. Cell. Biol., 1994, 14:416-426 (c-fos);
Akashi et al., Blood, 1994, 83:3182-3187 (GM-CSF etc.);
Nanbu et al., Mol. Cell. Biol., 1994, 14:4920-4920 (uPA);
Stoecklin et al., J. Biol. Chem., 1994, 269:28591-28597 (IL-3);
Lagnado et al., Mol. Cell. Biol., 1994, 14:7984-7995 (general);
Zhang et al., Mol. Cell. Biol., 1995, 15:2231-2244 (yeast);
Zubiaga et al., Mol. Cell. Biol., 1995, 15:2219-2230 (general);
Winstall et al., Mol. Cell. Biol., 1995, 15:3796-3804 (c-fos, GM-CSF);
Chen et al., Mol. Cell. Biol., 1995, 15:5777-5788 (c-fos, GM-CSF);
Chen et al., TIBS, 1995, 20:465-470 (review);
Levy et al., J. Biol. Chem., 1996, 271:2746-2753 (VEGF);
Kastelic et al., Cytokine, 1996, 8:751-761;
Crawford et al., J. Biol. Chem., 1997, 272:21120-21127 (TNFα);
Xu et al., Mol. Cell. Biol., 1997, 18:4611-4621 (general);
Danner et al., J. Biol. Chem., 1998, 273:3223-3229 (human β2-Adrenergic Receptor);
Lewis et al., J. Biol. Chem., 1998, 273:13781-13786 (TNFα);
Chen, C.-Y. and Shyu, A.-B., Mol. Cell. Biol., 1994, 14:8471-8482; and
Klausner, R. et al., Cell, 1993, 72:19-28.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an assay for identifying compounds which affect stability of mRNA. In accordance with an aspect of the present invention, there is provided a DNA expression vector comprising: a first DNA sequence comprising the coding sequence for one or more protein having a detectable signal; one or more 3' UTR sequence and one or more expression control sequence operatively associated with said coding sequence, and a heterologous instability sequence DNA inserted into said 3' UTR sequence comprising a second DNA sequence corresponding to one or more mRNA instability sequence derived from one or more naturally occurring genes.

In accordance with another aspect of the invention, there is provided a stably transfected cell line comprising: a DNA expression vector comprising a first DNA sequence encoding a first protein having a detectable signal, one or more 3' UTR sequence and one or more expression control sequence operatively associated with said first DNA sequence, and a heterologous instability sequence DNA inserted into said 3' UTR sequences, said instability sequence DNA comprising a second DNA sequence corresponding to one or more mRNA instability sequence derived from one or more naturally occurring genes; and a control DNA expression vector comprising a control DNA sequence encoding a second protein having a detectable signal, and one or more 3' UTR sequence and one or more expression control sequence operatively associated with said control DNA sequence.

In accordance with another aspect of the invention, there is provided a method of screening for one or more compound which affect mRNA stability comprising the steps of:
  i) providing a DNA expression vector, which in the absence of a test compound is capable of expressing a protein having a detectable signal, wherein the mRNA which is transcribed from said expression vector and encodes said protein comprises at least one copy of a heterologous mRNA instability sequence;
  ii) contacting said DNA expression vector with at least one test compound under conditions whereby, in the absence of the test compound, said DNA expression system is capable of expressing said protein having a detectable signal;
  iii) measuring said detectable signal; and
  iv) comparing the measured detectable signal with a control, wherein a decrease in the measured detectable signal compared to said control indicates a compound that decreases mRNA stability and an increase in the measured detectable signal compared to said control indicates a compound that increases mRNA stability.

In accordance with another aspect of the invention, there is provided a method for comparing the extent of mRNA degradation induced by two or more compounds comprising the steps of:
  i) providing a DNA expression vector, which in the absence of a test compound is capable of expressing a protein having a detectable signal, wherein the mRNA which is transcribed from said expression vector and encodes said protein comprises at least one copy of a heterologous mRNA instability sequence;
  ii) contacting said DNA expression vector separately with two or more test compounds under conditions whereby, in the absence of the test compounds, said DNA expression system is capable of expressing said protein having a detectable signal;
  iii) measuring said detectable signal in the presence of each test compound; and
  iv) comparing the measured detectable signals; wherein a lower measured detectable signal indicates a greater extent of mRNA degradation.

In accordance with another aspect of the invention, there is provided an assay system for screening for compounds which destabilise mRNA comprising:
  i) a DNA expression vector comprising a first DNA sequence encoding a first protein having a detectable signal, one or more 3' UTR sequence and one or more expression control sequence operatively associated with said DNA sequence, and a heterologous instability sequence DNA inserted into said 3' UTR sequences, said instability sequence DNA comprising a second DNA sequence corresponding to one or more mRNA instability sequence derived from one or more naturally occurring genes; and
  ii) a control DNA expression vector comprising a control DNA sequence encoding a control protein having a detectable signal, and one or more 3' UTR sequence and one or more expression control sequence operatively associated with said control DNA sequence.

In accordance with another aspect of the invention, there is provided a high throughput method for screening libraries of compounds to identify compounds that affect the stability of mRNA comprising:
  i) providing a stably transfected cell line comprising a DNA expression vector, which in the absence of a test compound is capable of expressing a protein having a detectable signal, wherein the mRNA which is transcribed from said expression vector and encodes said protein comprises at least one copy of a heterologous mRNA instability sequence;
  ii) inoculating wells of one or more multi-well plates comprising a growth medium with said cell line;
  iii) maintaining said one or more multi-well plates under conditions that allow cells of said cell line to grow and express said protein having a detectable signal;
  iv) contacting the cells with one or more test compound;
  v) measuring said detectable signal; and
  vi) comparing the measured detectable signal with a control;

wherein a decrease in the measured detectable signal compared to said control indicates a compound that decreases mRNA stability and an increase in the measured detectable signal compared to said control indicates a compound that increases mRNA stability.

In accordance with another aspect of the invention, there is provided a kit comprising an assay system for screening for compounds which destabilize mRNA, said assay system comprising:
  i) one or more DNA expression vector comprising a first DNA sequence encoding a protein having a detectable signal, one or more 3' UTR sequence and one or more expression control sequence operatively associated with said first DNA sequence, and a heterologous instability sequence DNA inserted into said 3' UTR sequences, said instability sequence DNA comprising a second DNA sequence corresponding to one or more mRNA instability sequence derived from one or more naturally occurring genes; and
  ii) a control DNA expression vector comprising a control DNA sequence encoding a second protein having a detectable signal, one or more 3' UTR sequence and one or more expression control sequence operatively associated with said control DNA sequence; and optionally
  iii) instructions for use.

BRIEF DESCRIPTION OF THE DRAWINGS

FIG. 1 shows the DNA sequence of IL-1β 3'UTR (SEQ ID NO:28);

FIG. 2 shows the 30 bp fragment used as a mRNA instability sequence in Example 1 (SEQ ID NOs: 29 and 30);

FIG. 9 shows the cDNA construct derived from the Human APP 3'UTR (SEQ ID NO:1);

FIG. 13 shows the cDNA construct derived from the Human TNFα 3'UTR (SEQ ID NO:5);

FIG. 15 shows the cDNA construct derived from the Human VEGF 3'UTR (SEQ ID NO:7);

DETAILED DESCRIPTION OF THE INVENTION

Figure 3A:
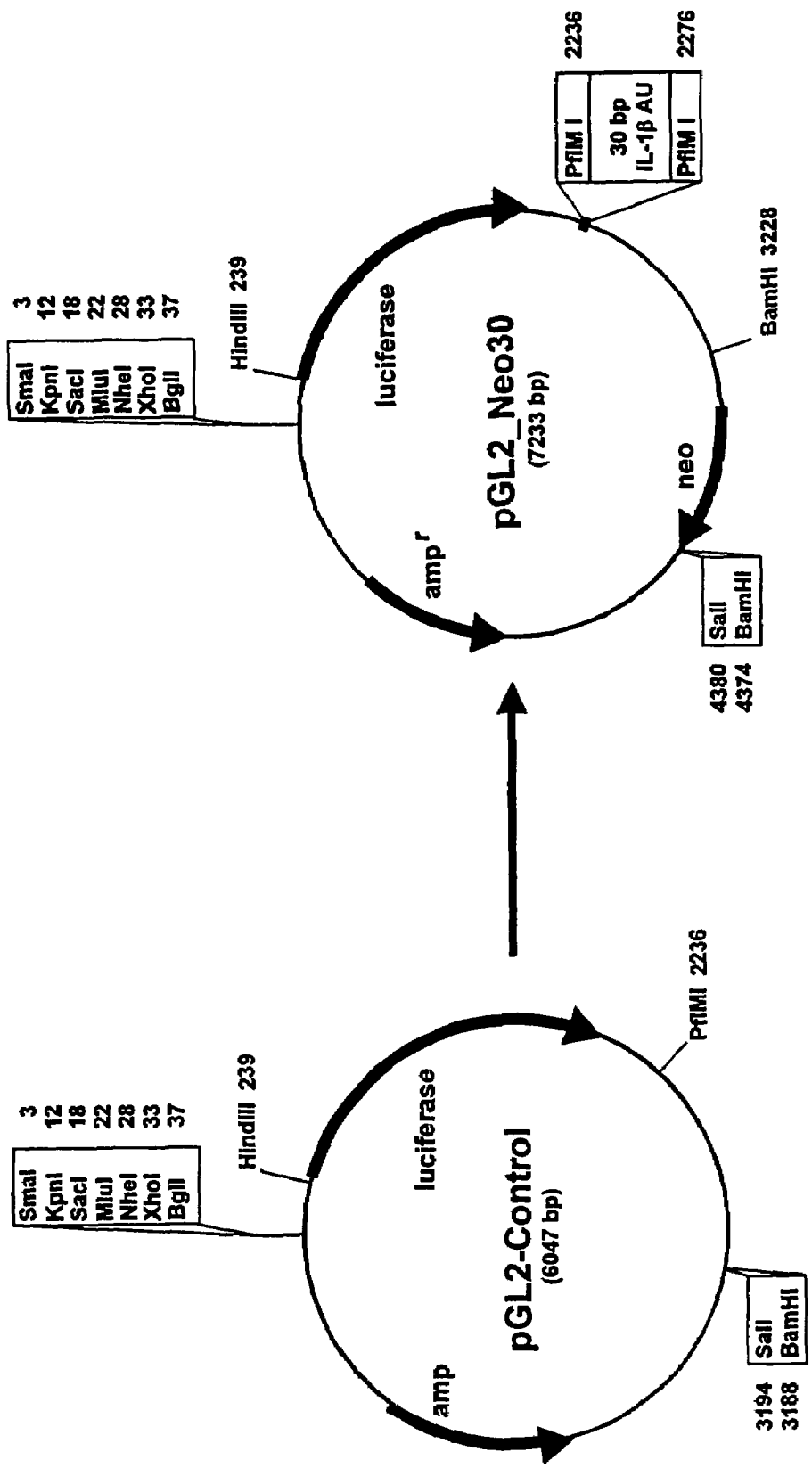
FIG. 3A shows plasmid diagrams for pGL2_Neo30 and pGL2-Control.

The present invention provides for DNA expression systems comprising a reporter gene in association with DNA corresponding to at least one mRNA instability sequence and optionally sequences that flank the instability mRNA. This DNA is referred to as the "instability sequence DNA" or "is DNA" and typically comprises a nucleotide sequence that is present in the 3'UTR or coding region of certain naturally occurring genes ("source genes") and which is known to affect the stability of the mRNA transcribed from the source gene. Thus, the isDNA incorporated into the expression systems of the invention can comprise a sequence corresponding to the entire 3'UTR of a source gene, or a substantial part of the 3' UTR or one or more fragment of the 3' UTR. The is DNA may comprise one or more instability sequence (and optionally their flanking regions) derived from a single source gene, or from a plurality of source genes. The expression systems of the present invention typically comprise a reporter gene together with appropriate 3' and 5' gene flanking sequences, including the 5' and 3' untranslated regions (UTRs). In the expression systems of the present invention, the is DNA is inserted into the 3' UTR associated with the reporter gene. Thus, the isDNA is heterologous to the DNA of the 3'UTR associated with the reporter gene.

The invention further provides for the use of the DNA expression systems in assays to identify compounds that affect mRNA stability. Accordingly, the present invention provides a method for the identification of a compound which affects mRNA stability in which the DNA expression system, which in the absence of the test compound is capable of expressing a protein having a detectable signal, is contacted with a test compound and the detectable signal is measured in the presence of the test compound and compared with a control.

The method of the invention is adapted for the identification of compounds which promote instability of mRNAs which contain mRNA instability sequences. The reporter gene assay may be used to screen individual compounds and libraries of compounds, including combinatorial compound libraries. The reporter gene assay may be used as a first line screening assay to identify lead compounds and may be used to compare or quantify the mRNA instability promoting activity of compounds, e.g. to compare compounds produced from medicinal chemistry lead optimisation/derivatisation programmes.

Compounds that promote instability of mRNAs containing mRNA instability sequences can be used to induce degradation of such mRNAs in a subject, thus preventing or reversing inappropriate mRNA accumulation and thereby decreasing or preventing unwanted protein expression, for example unwanted cytokine expression. Such compounds have potential pharmaceutical applications in the prophylaxis and/or treatment of diseases or medical conditions that involve inappropriate mRNA stabilisation and accumulation and resultant undesirable protein expression.

Unless defined otherwise, all technical and scientific terms used herein have the same meaning as commonly understood by one of ordinary skill in the art to which this invention belongs. Generally, the nomenclature used herein and the laboratory procedures in cell culture, molecular biology, screening methods, and nucleic acid chemistry, and compound identification described below are those well known and commonly employed in the art. Standard techniques are typically used for preparation of vectors, recombinant nucleic acid methods, cell culture and transformation.

The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., and Lakowicz, J. R. Principles of Fluorescence Spectroscopy, New York: Plenum Press (1983) for fluorescence techniques). Standard techniques are used for chemical syntheses, chemical analyses, and biological assays. As employed throughout the disclosure, the following terms, unless otherwise indicated, shall be understood to have the following meanings:

DEFINITIONS

The term "oligonucleotide," as used herein, refers to sequence of nucleotides that can be ribonucleic acid (RNA) or deoxyribonucleic acid (DNA).

The term "reporter gene," as used herein, refers to a gene encoding a detectable protein. The detectable protein encoded by the reporter gene may be, for example, a fluorescent protein or it may be capable of reacting with an appropriate substrate or other substance to give a detectable signal.

The term "detectable signal," as used herein, refers to a signal that can be detected directly or indirectly. Typically, the detectable signal can be detected by spectroscopic, photochemical, biochemical, immunochemical, or chemical means. The detectable signal may be produced directly or it may be produced indirectly by reaction or interaction with a suitable "conjugate" (for example, a substrate, antibody, ligand, and the like).

The term "test compound," as used herein, refers to a compound that can be tested according to the assays and methods of the invention and can include, but is not limited to, organometallic compounds, polynucleotides, oligonucleotides, peptides, proteins, organic compounds, metals, transitional metal complexes, and small molecules (for example, non-peptidic and non-oligomeric compounds).

The term "instability sequence" refers to a nucleotide sequence that is capable of modulating the stability of a mRNA. In the context of the present invention, "instability sequences" include nucleotide sequences that confer instability on a mRNA under normal physiological conditions, nucleotide sequences that confer instability on a mRNA under physiologically abnormal, or stress, conditions, as well as nucleotide sequences that have little, or no, effect on the stability of a mRNA under normal physiological conditions but increase the stability of the mRNA under certain stress conditions. Physiologically abnormal, or stress, conditions generally involve the presence, absence or shift of a controlling factor relative to normal physiological conditions.

The term "controlling factor" refers to modifiable factors including (but not limited to) oxygen, temperature, and light.

The terms "corresponds to" and "corresponding to," are used herein to describe the relationship between a DNA sequence and a RNA sequence wherein the DNA sequence is the direct counterpart of the RNA sequence and vice versa, i.e. the two sequences are identical with the exception that when a "T" base occurs in a DNA sequence it is replaced with a "U" base in the RNA counterpart sequence. For illustration, a RNA sequence "UAUAC" corresponds to a DNA sequence "TATAC." Likewise, a DNA sequence "GTTCA" corresponds to a RNA sequence "GUUCA."

"Naturally occurring" as used herein with reference to a gene, refers to the fact that the gene can be found in nature. For example, a gene that is present in an organism (including viruses) that can be isolated from a source in nature and which has not been intentionally modified by man in the laboratory is naturally occurring.

As used herein, the term "about" refers to a +/−10% variation from the nominal value. It is to be understood that such a variation is always included in any given value provided herein, whether or not it is specifically referred to.

Other chemistry terms herein are used according to conventional usage in the art, as exemplified by The McGraw-Hill Dictionary of Chemical Terms (ed. Parker, S., 1985, McGraw-Hill, San Francisco), incorporated herein by reference.

1. DNA Expression System

The DNA expression system of the present invention comprises a reporter gene associated with DNA corresponding to at least one mRNA instability sequence, i.e. instability sequence DNA (isDNA). The reporter gene and associated isDNA are typically comprised within a suitable vector which is used to transform an appropriate cell line in order to provide a means for expressing the protein encoded by the reporter gene. A single cell line can be transformed with one vector or it may be transformed with a combination of vectors. In the latter case, each vector can incorporate a different reporter gene and isDNA such that the cell line can subsequently be used in assays to identify the effect of a compound on the stability of a multiplicity of mRNAs.

1.1 isDNA Sequences

The isDNA included in the expression system of the invention comprises DNA corresponding to at least one mRNA instability sequence derived from one or more source gene. The isDNA may further comprise DNA corresponding to the regions that flank the mRNA instability sequence in the naturally-occurring source gene or mRNA transcribed therefrom. Thus, in one embodiment of the invention the isDNA is from about 10 to about 1500 nucleotides in length.

1.1.1 Source Genes

In accordance with the present invention, the isDNA comprises DNA corresponding to one or more mRNA instability sequence that is derived from one or more source gene, i.e. a gene known to contain sequences that affect the stability of the mRNA transcribed from the gene. As indicated above, mRNA instability sequences have been identified in the UTRs, in particular the 3' UTRs, of a large number of transiently expressed genes including, cytokines, chemokines, nuclear transcription factors, proto-oncogenes, immediate early genes, cell cycle controlling genes, oxygenases and genes involved in and controlling apoptosis. Such genes, therefore, can serve as source genes for the purposes of the present invention. Non-limiting examples of specific source genes from which mRNA instability sequences can be derived include the genes coding for APP, VEGF, bcl-2α, GM-CSF, c-fos, c-myc, c-jun, krox-20, nur-77, zif268, bcl-2, β-IFN, uPA, IL-1α, IL-1β, IL-2, IL-3, IL-4, IL-5, IL-6, IL-7, IL-8, IL-9, IL-10, IL-11, IL-13, TNFα, synl, β2-AR, E-selectin, VCAM-1, ICAM-1, Gro-α (melanoma growth stimulating activity alpha), Gro-β (MIP-2α), Gro-γ (MIP-2β), MMP-1, MMP-2, collagenases, P-glycoproteins (MDR), MRPs, Pγh1 (pf mdr), COXII, endothelial lipase, cholesterylester transfer protein, β-adrenergic receptor, MIP-1α, MIP-1β, MCP-1, MCP-2, nuclear factor of kappa light polypeptide gene enhancer in B-cells inhibitor alpha (NFKBIA), IFNγ inducible protein 10 kD (IP-10), cyclophilin F, IL-10 receptor alpha, AUF1, tristetraproline, and ubiquitin specific protease 18.

In addition, instability sequences have been identified within the coding region of certain genes. For example, two instability sequence regions have been found that affect the stability of c-myc mRNA; one is an AU-rich element found in the 3'-UTR and the other is an approximately 250 nucleotide region found within the coding region and referred to as a coding region instability determinant (CRD) (see, Bernstein et al., *Genes Dev.*, 1992, 6:642-654). Thus, for the purposes of the present invention, the c-myc gene would serve as the source of at least two different instability sequences.

In one embodiment of the present invention, a source gene is selected that contains mRNA instability sequences comprising one or more AU-rich element, or AREs. Examples of AREs include, but are not limited to, AUUUA; UAUUUAU; UUAUUUA(U/A)(U/A), and AUUUAUUUA. Non-limiting examples of source genes containing AREs suitable for the purposes of the present invention are provided in Table 1. The AREs found in these genes differ from each other by the arrangement and number of the basic AUUUA pentanucleotide consensus sequence as indicated in Table 1.

In another embodiment, a source gene is selected that comprises a coding region determinant (or CRD). In accordance with this embodiment, the source gene may also comprise one or more ARE.

A source gene may be selected that codes for a protein which is implicated in a disease of interest. Thus, for example, a mRNA instability sequence can be selected that is derived from a source gene which codes for a cytokine or oncogene involved in the aetiology of a particular disease process. Expression systems comprising isDNA corresponding to these mRNA instability sequences are useful for detecting compounds that destabilise the cytokine or oncogene mRNA and which thus, may be useful in the treatment of the associated disease process. For example, lead compounds for treatment of IL-1 mediated diseases, such as rheumatoid arthritis or osteoarthritis, may be detected using a DNA expression system comprising an IL-1 mRNA instability sequence. Diseases associated with increased stability of mRNAs from certain source genes are also indicated in Table 1.

TABLE 1

Examples of source genes whose mRNA contains ARE motifs and the diseases associated with increased stability of the mRNA

| Gene | Number of AU motifs in mRNA | Associated Disease |
| --- | --- | --- |
| IL-1β | 6 | Inflammation |
| TNFα | 9 | Inflammation, Cardiovascular |
| IL-6 | 6 | Inflammation |
| COX-2 | 12 | Inflammation |
| IL-2 | 7 | Organ rejection, Immune response |
| IL-3 | 6 | Cancer |
| GM-CSF | 8 | Cancer |
| K-Ras | 5 | Cancer |
| c-myc | 5 | Cancer |
| bcl-2α | 9 | Cancer |
| IL-8 | 9 | Inflammation, Angiogenesis |
| MIP-2α (Gro-β) | 10 | Inflammation, Immune response |
| VEGF | 10 | Cancer, Arteriosclerotic diseases |
| APP | 5 | Alzheimer's |
| E-selectin | 8 | Inflammation, Immune response |

1.1.2 mRNA Instability Sequences

The isDNA can comprise DNA corresponding to one mRNA instability sequence, or it can comprise DNA corresponding to two or more instability sequences. In accordance with one embodiment of the present invention, the isDNA comprises DNA corresponding to between one and about 12 mRNA instability sequences. The instability sequence may be an ARE, or a part thereof (e.g. normally containing at least 4 consecutive nucleotides from the AU-rich motif) in appropriate juxtaposition, normally together, e.g. as tandem repeats, or with other, e.g. intervening, nucleotide sequences. Alternatively, the instability sequence can be a CRD, or fragment thereof. Furthermore, the isDNA sequence can comprise both one or more ARE and one or more CRD, with or without their respective flanking sequences. In one embodiment, the isDNA can comprise one or more fragment of a CRD, in combination with an ARE encoding instability sequence.

In another embodiment of the invention, the mRNA instability sequences contain at least 1 ARE. In a further embodiment of the invention, the mRNA instability sequences contain at least 2 AREs. In a further embodiment of the invention, the mRNA instability sequences contain at least 3 AREs. In a further embodiment of the invention, the mRNA instability sequences contain at least 4 AREs. In a further embodiment of the invention, the mRNA instability sequences contain at least 5 AREs. In a further embodiment of the invention, the mRNA instability sequences contain at least 6 AREs. In a further embodiment of the invention, the mRNA instability sequences contain at least 7 AREs. In a further embodiment of the invention, the mRNA instability sequences contain at least 8 AREs. In a further embodiment of the invention, the mRNA instability sequences contain at least 9 AREs. In a further embodiment of the invention, the mRNA instability sequences contain at least 10 AREs. In a further embodiment of the invention, the mRNA instability sequences contain at least 11 AREs. In a further embodiment of the invention, the mRNA instability sequences contain as many as 12 AREs.

In an alternative embodiment of the invention, the instability sequence comprises at least one CRD of a source gene, together with relevant flanking regions. In another embodiment of the invention, the instability sequence may comprise at least one CRD without flanking regions. In yet another embodiment, the instability sequence may comprise one or more fragment of a CRD, with or without a flanking sequence.

Typically the mRNA instability sequence from which the isDNA is derived comprises at least about 10 and up to at least about 50 contiguous nucleotides. Thus, in one embodiment of the invention, the mRNA instability sequence comprises at least 10 contiguous nucleotides. In another embodiment of the invention, the mRNA instability sequence comprises at least 20 contiguous nucleotides. In a further embodiment of the invention, the mRNA instability sequence comprises at least 30 contiguous nucleotides. In a further embodiment of the invention, the mRNA instability sequence comprises at least 40 contiguous nucleotides. In a further embodiment of the invention, the mRNA instability sequence comprises at least 50 contiguous nucleotides.

As previously mentioned, the isDNA comprises DNA corresponding to at least one mRNA instability sequence derived from one or more source gene and can be from about 10 nucleotides in length to about 1500 nucleotides in length. In one embodiment of the invention, the isDNA is from about 20 to about 1200 nucleotides in length. It will be readily apparent to one skilled in the art that the length of the isDNA will depend on the number and type of instability sequences it comprises as well as whether any flanking regions are to be included. Thus, in another embodiment of the invention, the isDNA is from about 20 to about 200 nucleotides in length. In yet another embodiment of the invention, the isDNA is from about 20 to about 500 nucleotides in length. In an alternative embodiment, the isDNA is from about 500 to about 1500 nucleotides in length. In a further embodiment, the isDNA is from about 500 to about 1200 nucleotides in length.

In another embodiment of the present invention, the mRNA instability sequence contains an arrangement of identical motifs or a combination of different motifs selected from the group of: AUUUA; UAUUUAU; UUAUUUA(U/A)(U/A), and AUUUAUUUA.

As indicated above, instability sequences contemplated by the present invention include nucleotide sequences that have little, or no, effect on the stability of a mRNA under normal physiological conditions but increase the stability of the mRNA under certain stress conditions. For example, the VEGF hypoxia domain found in the 3' UTR of the human VEGF gene is an ARE that increases the stability of VEGF mRNA in the presence of diminished oxygen, acting to stabilize the mRNA (see, Claffey et al., Mol. Biol. Cell, 1998, 9:469-481). In one embodiment of the present invention, the isDNA comprises all, or a part, of the VEGF hypoxia domain.

The isDNA of the present invention may be derived as a restriction fragment from the 3' UTR or coding region of an appropriate source gene, or as a de novo synthesised nucleotide sequence comprising the one or more mRNA instability sequence, for example, as a PCR or RT-PCR generated sequence. The isDNA can comprise a sequence corresponding to the entire/whole 3' UTR of an appropriate source gene sequence, which contains one or more mRNA instability sequence together with relevant flanking regions, or it can comprise a substantial part of the 3' UTR of the source gene or one or more fragment of the 3' UTR of the source gene. Similarly, when an isDNA comprises one or more CRD from a source gene, the isDNA can comprise a substantial portion of the coding sequence that contains the one or more CRD with relevant flanking sequence, or it can comprise a smaller portion of the coding region that comprises the entire CRD, with or without relevant flanking sequences, or it can comprise a portion of the coding region that comprises a fragment of a CRD, with or without flanking sequences.

In one embodiment of the present invention, the expression systems comprise isDNA sequences corresponding to one or more mRNA instability sequence that are derived from the 3'UTR or coding region of one or more source gene selected from the group of: APP, bcl-2α, c-myc, TNFα, IL-1β and VEGF mRNAs. In another embodiment, the one or more source gene indicated above are human genes. Representative sequences corresponding to parts of the 3'UTRs of Human APP, bcl-2α, c-myc, TNFα, IL-1β, VEGF, and the Human VEGF hypoxia domain, are provided in Table 2 as SEQ ID NOs: 1, 2, 3, 4, 5, 6, 7 and 8. Thus, in another embodiment of the invention the isDNA sequences included in the expression systems comprise the entire sequence as set forth in any one of SEQ ID NOs: 1, 2, 3, 4, 5, 6, 7 or 8. In a further embodiment of the invention the isDNA sequences included in the expression systems comprise a fragment of the sequence as set forth in any one of SEQ ID NOs: 1, 2, 3, 4, 5, 6, 7 or 8. In a further embodiment of the present invention, the isDNA sequences included in the expression systems comprise at least 10 consecutive nucleotides as set forth in any one of SEQ ID NOs: 1, 2, 3, 4, 5, 6, 7 or 8.

TABLE 2

Examples of source gene 3' UTR sequences

| Seq. ID No. | Gene designation | Sequence | | | | |
|---|---|---|---|---|---|---|
| 1. | Human APP 3' UTR | gcggccgcca | cagcagcctc | tgaagttgga | cagcaaaacc | attgcttcac tacccatcgg |
| | | tgtccattta | tagaataatg | tgggaagaaa | caaacccgtt | ttatgattta ctcattatcg |
| | | ccttttgaca | gctgtgctgt | aacacaagta | gatgcctgaa | cttgaattaa tccacacatc |
| | | agtaatgtat | tctatctctc | tttacatttt | ggtctctata | ctacattatt aatgggtttt gtgtactgta |
| | | aagaatttag | ctgtatcaaa | ctagtgcatg | aatagattct | ctcctgatta tttatcacat |
| | | agccccttag | ccagttgtat | attattcttg | tggtttgtga | cccaattaag tcctacttta catatgcttt |
| | | aagaatcgat | gggggatgct | tcatgtgaac | gtgggagttc | agctgcttct cttgcctaag |
| | | tattcctttc | ctgatcacta | tgcattttaa | agttaaacat | ttttaagtat ttcagatgct ttagagagat |
| | | ttttttttcc | atgactgcat | tttactgtac | agattgctgc | ttctgctata tttgtgatat aggaattaag |
| | | aggatacaca | cgtttgtttc | ttcgtgcctg | ttttatgtgc | acacattagg cattgagact |
| | | tcaagctttt | ctttttttgt | ccacgtatct | ttgggtcttt | gataaagaaa agaatccctg ttcattgtaa |
| | | gcactttac | ggggcgggtg | gggaggggtg | ctctgctggt | cttcaattac caagaattct |
| | | ccaaaacaat | tttctgcagg | atgattgtac | agaatcattg | cttatgacat gatcgctttc |
| | | tacactgtat | tacataaata | aattaaataa | aataaccccg | ggcaagactt ttctttgaag |
| | | gatgactaca | gacattaaat | aatcgaagta | attttgggtg | gggagaagag gcagattcaa |
| | | ttttctttaa | ccagtctgaa | gtttcattta | tgatacaaaa | gaagatgaaa atggaagtgg |
| | | caatataagg | ggatgaggaa | ggcatgcctg | gacaaaccct | tcttttaaga tgtgtcttca |
| | | atttgtataa | aatggtgttt | tcatgtagcg | gccgc | |
| 2. | Human bcl-2α long 3' UTR | gcggccgctg | aagtcaacat | gcctgcccca | aacaaatatg | caaaaggttc actaaagcag |
| | | tagaaataat | atgcattgtc | agtgatgtac | catgaaacaa | agctgcaggc tgtttaagaa |
| | | aaataacac | acatataaac | atcacacaca | cagacagaca | cacacacaca caacaattaa |
| | | cagtcttcag | gcaaaacgtc | gaatcagcta | tttactgcca | aagggaaata tcatttattt |
| | | tttacattat | taagaaaaaa | agatttattt | atttaagaca | gtcccatcaa aactcctgtc |
| | | tttggaaatc | cgaccactaa | ttgccaagca | ccgcttcgtg | tggctccacc tggatgttct |
| | | gtgcctgtaa | acatagattc | gctttccatg | ttgttggccg | gatcaccatc tgaagagcag |
| | | acggatggaa | aaaggacctg | atcattgggg | aagctggctt | tctggctgct ggaggctggg |
| | | gagaaggtgt | tcattcactt | gcatttcttt | gccctggggg | ctgtgatatt aacagaggga |
| | | gggttcctgt | gggggaagt | ccatgcctcc | ctggcctgaa | gaagagactc tttgcatatg |
| | | actcacatga | tgcatacctg | gtgggaggaa | aagagttggg | aacttcagat ggacctagta |
| | | cccactgaga | tttccacgcc | gaaggacagc | gatgggaaaa | atgcccttaa atcataggaa |
| | | agtattttt | taagctacca | attgtgccga | gaaaagcatt | ttagcaattt atacaatatc |
| | | atccagtacc | ttaagccctg | attgtgtata | ttcatatatt | ttggatacgc acccccaac |
| | | tcccaatact | ggctctgtct | gagtaagaaa | cagaatcctc | tggaacttga ggaagtgcgg ccgc |

TABLE 2-continued

Examples of source gene 3' UTR sequences

| Seq. ID No. | Gene designation | Sequence |
|---|---|---|

3. Human bcl-2α short 3' UTR

```
gcggccgctg aagtcaacat gcctgcccca acaaatatg caaaaggttc actaaagcag
tagaaataat atgcattgtc agtgatgtac catgaaacaa agctgcaggc tgtttaagaa
aaaataacac acatataaac atcacacaca cagacagaca cacacacaca caacaattaa
cagtcttcag gcaaaacgtc gaatcagcta tttactgcca aagggaaata tcatttattt
tttacattat taagaaaaaa agatttattt atttaagaca gtcccatcaa aactcctgtc
tttggaaatc cgaccactaa ttgccaagca ccgcttcgtg tggctccacc tggatgttct
gtgcctgtaa acatagattc gctttccatg ttgttggccg gatcaccatc tgaagagcag
acggatgaa aaaggacctg atcattgggg aagctggctt tctggctgct ggaggctggg
gagaaggtgt tcattcactt gcatttcttt gccctggggg ctgtgatatt aacagaggga
gggttcctgt gggggaagt ccatgcctcc ctggcctgaa gaagagactc tttgcatatg
actcacatga tgcatacctg gtgggaggaa aagagttggg aacttcagat ggacctagta
cccactgaga tttccacgcc gaaggacagc gatgggaaaa atgcggccgc
```

4. Human c-myc 3' UTR

```
gcggccgctc ggagcttttt tgccctgcgt gaccagatcc cggagttgga aaacaatgaa
aaggccccca aggtagttat ccttaaaaaa gccacagcat acatcctgtc cgtccaagca
gaggagcaaa agctcatttc tgaagaggac ttgttgcgga acgacgaga acagttgaaa
cacaaacttg aacagctacg gaactcttgt gcgtaaggaa aagtaaggaa acgattcct
tctgacgaaa atgtcctgag caatcaccta tgaacttgtt tcaaatgcat gatcaaatgc
aacctcacaa ccttggctga gtcttgagac tgaaagattt agccataatg taaactgcct
caaattggac tttgggcata aaagaacttt tttatgctta ccatctttt tttttcttta acagatttgt
atttaagaat tgttttaaaa aaattttaag atttacacaa tgtttctctg taaatattgc cattaaatgt
aaataacttt aataaaacgt ttatagcagt tacacagaat ttcaatccta gtatatagta
cctagtatta taggtactat aaaccctaat ttttttttatt taagtacatt ttgctttta aagttgattt
ttttctattg tttttagaaa aaataaaata actggcaaat atatcattga gccatatg
```

5. Human TNFα 3' UTR

```
gcggccgctg aggaggacga acatccaacc ttcccaaacg cctcccctgc cccaatccct
ttattacccc ctccttcaga cacccctcaac ctcttctggc tcaaaaagag aattgggggc
ttagggtcgg aacccaagct tagaacttta agcaacaaga ccaccacttc gaaacctggg
attcaggaat gtgtggcctg cacagtgaag tgctggcaac cactaagaat tcaaactggg
gcctccagaa ctcactgggg cctacagctt tgatccctga catctggaat ctggagacca
gggagccttt ggttctggcc agaatgctgc aggacttgag aagacctcac ctagaaattg
acacaagtgg accttaggcc ttcctctctc cagatgtttc cagacttcct tgagacacgg
agcccagccc tcccccatgga gccagctccc tctatttatg tttgcacttg tgattattta ttatttattt
attatttatt tatttacaga tgaatgtatt tatttgggag accggggtat cctggggac
ccaatgtagg agctgccttg gctcagacat gttttccgtg aaaacggagc tgaacaatag
gctgttccca tgtagccccc tggcctctgt gccttctttt gattatgttt tttaaaatat ttatctgatt
aagttgtcta aacaatgctg atttggtgac caactgtcac tcattgctga gcctctgctc
cccaggggag ttgtgtctgt aatcgcccta ctattcagtg gcgagaaata agtttgctt catatg
```

TABLE 2-continued

Examples of source gene 3' UTR sequences

| Seq. ID No. | Gene designation | Sequence |
|---|---|---|
| 6. | Human IL-1β 3' UTR | gcggccgcta aagagagctg tacccagaga gtcctgtgct gaatgtggac tcaatccta<br>gggctggcag aaagggaaca gaaaggtttt tgagtacggc tatagcctgg actttcctgt<br>tgtctacacc aatgcccaac tgcctgcctt agggtagtgc taagaggatc tcctgtccat<br>cagccaggac agtcagctct ctcctttcag ggccaatccc cagccctttt gttgagccag<br>gcctctctca cctctcctac tcacttaaag cccgcctgac agaaaccacg gccacatttg<br>gttctaagaa accctctgtc attcgctccc acattctgat gagcaaccgc ttccctattt<br>atttatttat ttgtttgttt gttttattca ttggtctaat ttattcaaag ggggcaagaa gtagcagtgt<br>ctgtaaaaga gcctagtttt taatagctat ggaatcaatt caatttggac tggtgtgctc<br>tctttaaatc aagtccttta attaagactg aaaatatata agctcagatt atttaaatgg gaatatttat<br>aaatgagcaa atatcatact gttcaatggt tctgaaataa acttcaccat atg |
| 7. | Human VEGF 3' UTR | gcggccgcat tgctgtgctt tggggattcc ctccacatgc tgcacgcgca tctcgccccc<br>aggggcactg cctggaagat tcaggagcct gggcggcctt cgcttactct cacctgcttc<br>tgagttgccc aggaggccac tggcagatgt cccggcgaag agaagagaca cattgttgga<br>agaagcagcc catgacagct ccccttcctg ggactcgccc tcatcctctt cctgctcccc<br>ttcctggggt gcagcctaaa aggacctatg tcctcacacc attgaaacca ctagttctgt<br>ccccccagga gacctggttg tgtgtgtgtg agtggttgac cttcctccat cccctggtcc<br>ttcccttccc ttcccgaggc acagagagac agggcaggat ccacgtgccc attgtggagg<br>cagagaaaag agaaagtgtt ttatatacgg tacttattta atatcccttt ttaattagaa<br>attaaaacag ttaatttaat taaagagtag ggttttttt cagtattctt ggttaatatt taatttcaac<br>tatttatgag atgtatcttt tgctctctct tgctctctta tttgtaccgg ttttgtata taaaattcat<br>gtttccaatc tctctctccc tgatcggtga cagtcactag cttatcttga acagatattt<br>aatttgcta acactcagct ctgccctccc cgatcccctg gctccccagc acacattcct<br>ttgaaataag gtttcaatat acatctacat actatatata tatatttggc aacttgtatt tgtgtgtata<br>tatatatata tatgtttatg tatatatgtg attctgataa aatagacatt gctattctgt tttttatatg<br>taaaaacaaa acaagaaaaa atagagaatt ctacatacta aatctctctc cttttttaat tttaatattt<br>gttatcattt atttattggt gctactgttt atccgtaata attgtgggga aaagatatta<br>acatcacgtc tttgtctcta gtgcagtttt tcgagatatt ccgtagtaca tatttatttt taaacaacga<br>caaagaaata cagaacatat g |
| 8. | Human VEGF hypoxia domain 3' UTR | gcggccgcat tcctgtagac acacccaccc acatacatac atttatatat atatatatta<br>tatatatata aaaataaata tctctatttt atatatataa aatatatata ttctttttt aaattaacag<br>tgctaatgtt attggtgtct tcactggatg aacatatg |

1.1.3 Flanking Sequences

By considering the uniqueness of ARE and CRD flanking sequences, one approach of achieving selectivity for cellular processes involving AU-rich motifs may be through the existence of different instability sequence binding proteins. Cytoplasmic mRNA-binding proteins, which interact with AREs, are thought to act as regulatory trans-factors. Their binding to mRNA shows either stabilizing or destabilizing effects.

Based on the above, the skilled artisan would understand that a number of motifs as well as lengths of the instability sequence may be considered in the preparation of a DNA expression system for the identification of compounds affecting mRNA stability. One would further understand that the flanking sequences may comprise either coding or non-coding sequences depending on the nature of sequence they flank. The present invention thus contemplates isDNA that comprises DNA corresponding to one or more mRNA instability sequence together with sequences that flank the mRNA in the naturally occurring source gene or mRNA. Expression systems comprising isDNA that include these flanking sequences can be used to screen for compounds with specificity for the source gene/mRNA from which the instability sequences and flanking sequences were derived.

Flanking sequences can be included in the expression systems of the invention by deriving the sequence of the isDNA from the entire 3'UTR sequence of the source gene, or from a substantial portion of the 3'UTR sequence. Furthermore, the isDNA may, in addition to the entire or substantial 3'UTR, include one or more CRD, or fragments thereof, from the coding region of the same or a different source gene.

While the entire/whole 3'UTR sequence typically refers to a region from about the stop codon up to or including the polyadenylated sequence, substantial portions of the 3'UTR may include, but are not limited to, sequences comprising from about 10 up to about 600 nucleotides in length. Thus, in other embodiments of the invention the substantial portions of the 3'UTR include sequences comprising from about 10 to about 100 or from about 10 to about 200, or from about 20 to about 100, or from about 20 to about 200, or from about 20 to about 600 nucleotides in length, in the region from about the stop codon up to or including the polyadenylated sequence.

Similarly, the isDNA can comprise a "substantial portion" of the coding region together with one or more CRD. The coding region is defined as the region between the start and the stop codon of a gene. Substantial portions of the coding region can include, but are not limited to, sequences comprising from about 10 up to about 600 nucleotides in length that incorporate at least one CRD. In one embodiment of the invention, a substantial portion of the coding region includes sequences comprising from about 10 to about 100 nucleotides that incorporate at least one CRD. In other embodiments, a substantial portion of the coding region includes sequences from about 10 to about 200, or from about 20 to about 100, or from about 20 to about 200, or from about 20 to about 600 nucleotides that incorporate at least one CRD.

Fragments of the 3'UTR and coding sequences described above are also within the scope of the invention. Thus, in one embodiment of the present invention, the fragments comprise at least 8 contiguous nucleotides. In other embodiments of the invention, the fragments comprise at least 10, or at least 15, or at least 20, or at least 25, or at least 30, or at least 35, or at least 40, or at least 45, or at least 50 contiguous nucleotides.

One skilled in the art will appreciate that flanking sequences that are substantially identical to those found in the naturally occurring gene may still confer specificity on the mRNA instability sequence(s). The present invention, therefore, contemplates 3'UTR fragments that are substantially identical to a region of the 3'UTR of the source gene provided that the fragments comprise at least one mRNA instability sequence. Thus, in one embodiment of the invention, nucleotide fragments of the present invention include sequence lengths that are at least 10% to at least 90% of the 3'UTR of a source gene provided that the fragments include at least one mRNA instability sequence. In another embodiment of the invention, the nucleotide fragment of the present invention comprises a sequence length that is at least 10% of the length of the 3'UTR of a source gene. In a further embodiment of the invention, the nucleotide fragment of the present invention comprises a sequence length that is at least 20% of the length of the 3'UTR of a source gene. In a further embodiment of the invention, the nucleotide fragment of the present invention comprises a sequence length that is at least 30% of the length of the 3'UTR of a source gene. In a further embodiment of the invention, the nucleotide fragment of the present invention comprises a sequence length that is at least 40% of the length of the 3'UTR of a source gene. In a further embodiment of the invention, the nucleotide fragment of the present invention comprises a sequence length that is at least 50% of the length of the 3'UTR of a source gene. In a further embodiment of the invention, the nucleotide fragment of the present invention comprises a sequence length that is at least 60% of the length of the 3'UTR of a source gene. In a further embodiment of the invention, the nucleotide fragment of the present invention comprises a sequence length that is at least 70% of the length of the 3'UTR of a source gene. In a further embodiment of the invention, the nucleotide fragment of the present invention comprises a sequence length that is at least 80% of the length of the 3'UTR of a source gene. In a further embodiment of the invention, the nucleotide fragment of the present invention comprises a sequence length that is at least 90% of the length of the 3'UTR of a source gene.

In other embodiments of the invention, the fragments of the invention have at least 60%, or at least 70%, or at least 75%, or at least 80%, or at least 85%, or at least 90%, or at least 95%, or at least 97.5%, or at least 99% sequence identity with that of the 3'UTR or coding region, provided that the fragments include at least one instability sequence together with sequences that flank the instability sequence.

1.2 Efficacy of Instability Sequences

Provided with the above description, a skilled artisan could readily design a specific 3'UTR instability sequence for use in the DNA expression vectors of the invention for identifying destabilising compounds. Such an instability sequence would comprise at least one mRNA instability sequence and, where appropriate, sequences that confer compound-binding specificity flanking the mRNA instability sequence.

In order to test the efficacy of a 3'UTR instability sequence of the invention, analyses including gene expression studies are contemplated. In addition, other analyses familiar to a worker skilled in the art are understood, for example, RT-PCR, real time RT-PCR, Northern blot analysis, RNase protection, dot-blot or slot blot analysis, and microarray-based technologies. Other analyses may further involve testing with compounds known for their ability to cause mRNA instability. For example, a compound known to cause aberrant mRNA instability can be used in serial analysis of gene expression (SAGE) studies, in order to profile the 3'UTRs of the invention. Compounds capable of influencing mRNA stability include dexamethasone, tocopherol, retinoic acid, thalidomide, cyclosporin A, and radicicol analog A (RAA). RAA appears to promote the degradation of a number of mRNAs, including proto-oncogenes that contain the Shaw-Kamen box or AUUUA motif in their 3'UTRs.

1.3 Reporter Genes

A variety of reporter genes can be used in the expression systems of the present invention, provided that the gene encodes a detectable protein. In accordance with the present invention, a detectable protein is one that is capable of producing a detectable signal either directly (for example, a fluorescent signal, a change in absorbance, a phosphorescent signal, drug resistance or sensitivity, auxotrophism, and the like) or by reaction or interaction with a suitable "conjugate" (for example, a substrate, antibody, ligand, and the like). If necessary the conjugate can be labelled to permit detection.

Various reporter genes are known in the art (see, for example, Molecular Cloning: A Laboratory Manual, 2nd Ed., ed. by Sambrook, et al., Cold Spring Harbor Laboratory Press: 1989; various volumes of Methods in Enzymology, Academic Press, Inc., N.Y.; Ausubel et al. Current Protocols in Molecular Biology, John Wiley & Sons, Inc., New York, 1999 and updates). Examples of suitable reporter genes include, but are not limited to, those encoding enzymes, such as kinases, phosphatases (including alkaline phosphatase (AP and secreted alkaline phosphatase (SEAP)), luciferases, β-galactosidase, reductases, synthases, horseradish peroxidase, chloramphenicol transferase, glucose oxidase, synthetases and those encoding fluorescent or phosphorescent proteins, such as green fluorescent protein or a derivative thereof (such as red fluorescent protein, reef coral fluorescent protein, enhanced fluorescent proteins and destabilised fluorescent proteins). When the reporter gene encodes an enzyme, the enzyme itself may be detectable or the activity of the enzyme may be used to indirectly measure the level of the enzyme.

In one embodiment of the present invention, the reporter gene encodes an enzyme. In another embodiment of the invention, the reporter gene encodes a luciferase protein or a β-galactosidase protein. Luciferases are known in the art and can be derived from organisms such as the North American firefly, *Photinus pyralis*; the sea pansy, *Renilla reniformis*; and the bacterium, *Vibrio fischeri*.

1.4 Expression Vectors

Those skilled in the field of molecular biology will understand that a wide variety of expression vectors can be used to provide the DNA expression system of the invention. For example, a number of vectors suitable for stable transfection of cells are available to the public, see, e.g., Pouwels et al.; methods for constructing such cell lines are also publicly available, e.g., in Ausubel et al. The vector may be, for example, in the form of a plasmid, a viral particle, a phage, etc. Such vectors include, but are not limited to, chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, other vectors or plasmids may be used as long as they are replicable and viable in the host.

The appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The expression vectors of the present invention comprise a reporter gene operatively linked to an appropriate expression control sequence(s) to direct mRNA synthesis. As representative examples of such promoters, there may be mentioned: LTR or SV40 promoter, the *E. coli* lac or trp, the phage lambda $_P$L promoter and other promoters known to control expression of genes in prokaryotic or eukaryotic cells or their viruses. The vector may also include appropriate sequences for amplifying expression. The invention further provides a reporter gene DNA expression system comprising a gene coding for expression of a protein having a detectable signal, wherein the gene comprises DNA coding for the amino acid sequence of the protein together with associated 5' and 3' UTR sequences comprising appropriate expression control including promoter and/or enhancer regions, and an isDNA sequence. Appropriate choice of promoter/enhancer sequences and other expression control sequences is a matter well within the ambit of the skilled worker in the art, and does not form a substantive part of the invention. Thus, for instance, for expression in mammalian cells a viral promoter such as an SV40, CMV or HSV-I promoter may be used.

In addition, the expression vectors may contain a gene to provide a phenotypic trait for selection of transformed host cells such as dihydrofolate reductase, hygromycin B or neomycin resistance for eukaryotic cell culture, or such as tetracycline or ampicillin resistance in *E. coli*.

The isDNA is typically inserted into the 3' UTR of the reporter gene. Thus for example, the isDNA sequence is inserted into a suitable restriction site in the 3' UTR of the native reporter gene. Appropriate restriction enzyme sites may be introduced into the 3'UTR sequence and/or the isDNA sequence using standard techniques known in the art in order to permit insertion of the isDNA into the reporter gene 3'UTR.

1.5 Host Cells

Host cells may be genetically engineered (transduced or transformed or transfected) with the expression vectors of this invention. The engineered host cells can be cultured in conventional nutrient media modified as appropriate for activating promoters, or selecting transformants. The culture conditions, such as temperature, pH and the like, are those previously used with the host cell selected for, and will be apparent to the ordinarily skilled artisan. The DNA expression system may be a cell based expression system, conveniently in the form of a suitably transformed cell line, like a stably transformed cell line. The host cell may be an eukaryotic or prokaryotic host cell.

As representative examples of appropriate hosts, there may be mentioned: bacterial cells, such as *E. coli, Salmonella typhimurium, Streptomyces*; fungal cells, such as yeast; insect cells, such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

The host cell may be of the same general cell type as the cells which express the protein which is coded for by the mRNA which it is desired to destabilise. Thus for instance, if the assay of the invention is to be used for the identification of compounds which destabilise the mRNA coding for a cytokine, the host cell used may be a cell or cell line which is of the same or similar cell type to the cells which normally produce the cytokine in question. For example, monocyte or monocyte-like cell lines (such as THP-1) may be used as host cells for assaying for compounds which destabilise cytokine, e.g. IL-1β, mRNA. Cell lines useful for oncogene and other cancer related gene mRNA instability assays are, e.g. COLO 205, KB-31, KB-8511, DU145, HCT116, MCF7, MCF7/ADR, MDA-MB-231, MDA-MB-435 and MDA-MB-435/TO. Cell lines for use as the host cells in assays of the invention for identification of compounds which destabilise cytokine, e.g. IL-1β, mRNA are the THP-1 cell line (for instance as described by Auwerx J., 1991, Experientia, 47: 22-30) and similar monocytic, e.g. human leukaemia, cell lines.

Although the mechanism of mRNA destabilisation, and the role of mRNA instability sequences in this, is not fully understood, it is clear that the presence of other factors besides the destabilising compound and the mRNA instability sequence are required for mRNA destabilisation to take place; for instance, as discussed in previously identified literature references. In one embodiment of the present invention, therefore, a host cell is selected that provides for such other factors and complements or completes the interaction of the compound and the mRNA instability sequence to effect destabilisation of the mRNA. The transformed host cells may be stimulated or otherwise activated to enhance mRNA destabilisation, e.g. to provided enhanced levels of the cellular factors required for mRNA destabilisation. For example, improved results may be obtained in the assay of the invention if differentiated transformed host cells are used. For instance, in the case of transformed THP-1 cells, good results can be obtained if the transformed THP-1 cells are grown, differentiated and stimulated with γIFN and LPS as is normal for THP-1 cells, e.g. as described hereinafter in the Examples.

2. Assays and Methods for Identifying Compounds that Affect the Stability of mRNA In another embodiment of the invention an assay system for the identification of compounds which destabilise mRNA comprising; a reporter gene DNA expression system as defined above, and a control DNA expression system which comprises; a gene coding for expression of the protein having the detectable signal, wherein the gene comprises DNA coding for the amino acid sequence of the protein together with associated 5' and 3' UTR sequences comprising appropriate expression control elements but lacking a functional mRNA instability sequence is provided for.

Both the reporter gene DNA expression system and the control DNA expression system may be in the form of stably transfected cell lines.

Alternatively, the reporter gene expression system may be tested in the presence and absence of the test compound, testing in the absence of the test compound being used as the control. In another embodiment of the invention a control DNA expression system may also be present in the same cell line as the reporter gene DNA expression system. The control DNA expression system in this case would code for a detectable protein which is different than the protein coded for by the reporter gene expression system, and as before, the control DNA expression system lacks any functional mRNA instability sequence.

In the assay of the invention the presence of a compound which destabilises mRNA is indicated by a decrease in the magnitude of the detectable signal given by the protein produced from the expression system in the presence of the compound as compared with a control; destabilisation of the reporter gene mRNA by the compound leads to a decrease in expression of the protein and thus a decrease in the magnitude of the signal. A suitable control for use in the assay of the invention comprises a DNA expression system which corresponds to the reporter gene DNA expression system, i.e. contains sequence coding for expression of the detectable protein but which does not contain sequence corresponding to a mRNA instability sequence. The control DNA expression system may be identical to the reporter gene expression system except that the DNA corresponding to the mRNA instability sequence has been removed, deleted or otherwise disabled as a mRNA instability sequence. The control DNA expression system may also be in the form of a transformed cell line, typically a stably transformed cell line derived from the same host cell line, e.g. a THP-1 cell line, as the reporter gene transformed cell line.

The DNA expression system of the present invention can be used for screening compounds capable of destabilising mRNA. Thus, in one embodiment of the invention there is provided a method for the identification and screening of compounds which induce mRNA degradation comprising: contacting a compound with a DNA expression system which in the absence of the compound is capable of expressing a protein having a detectable signal, wherein the mRNA which codes for the protein and which is transcribed from the expression system comprises at least one copy of a mRNA instability sequence, measuring the detectable signal in the presence of the test compound and comparing the result obtained with a control.

For example, compounds capable of destabilising mRNA can be identified by culturing cells stably transfected with a DNA expression vector of the invention in a multiwell format. After an overnight incubation, compounds being screened for their ability to destabilise mRNA can be added to the wells at an appropriate concentration, or range of concentrations, and the treated cells incubated in the presence of the compound(s) for a suitable period (for example, between about 4 and about 16 hours). Following incubation, any reagents required to detect the signal produced by the reporter gene in the DNA expression system are added to the wells and the amount of signal generated in each well is measured (for example, by use of a multi-plate reader in conjunction with an appropriate detector). The amount of signal is then compared to a control, for example, cells treated with the solute or culture medium alone, in order to determine the efficacy of the test compound with reference to the control.

It will be understood by a worker skilled in the art that, for those expression systems comprising an instability sequence that does not affect the stability of a mRNA under normal physiological conditions but increases its stability under certain stress conditions, the cells comprising the expression system must be subjected to the stress conditions prior to addition of the test compound(s). Thus, for example, for an expression system comprising the VEGF hypoxia domain, the cells must be subjected to low oxygen conditions prior to addition of the test compound, i.e. the controlling factor (oxygen) must be reduced prior to testing the compound for its ability to destabilise the mRNA.

In another embodiment of the invention a method for the comparison of compounds which induce mRNA degradation, comprising separately contacting the compounds with a DNA expression system which in the absence of the compounds is capable of expressing a protein having a detectable signal, wherein the mRNA which codes for the protein and which is transcribed from the expression system comprises at least one copy of a mRNA instability sequence, measuring the detectable signal in the presence of each test compound and comparing the signals obtained is provided for. This method compares the extent of mRNA degradation induced by two or more compounds, with the compound whose presence results in a lower measured detectable signal inducing a greater extent of mRNA degradation.

Methods of detecting and/or measuring detectable signals produced by reporter genes are well known in the art and extensively described in the relevant literature. The method employed will be dependent on the chosen reporter gene and selection of an appropriate method is within the ordinary skills of a worker in the art. As indicated above, the detectable signal may be produced directly by the protein encoded by the reporter gene or it may be produced indirectly.

One skilled in the art will understand that directly detectable signals may require additional components, such as substrates, triggering reagents, light, and the like to enable detection of the signal. Indirectly detectable signals typically involve the use of a "conjugate" that specifically binds to the detectable protein and which is attached or coupled to a directly detectable label. Coupling chemistries for synthesizing such conjugates are well-known in the art. Binding between the detectable protein and the conjugate is typically chemical or physical in nature.

Examples of such binding pairs include, but are not limited to, antigens and antibodies; avidin/streptavidin and biotin; haptens and antibodies specific for haptens; receptors and receptor substrates; enzymes and enzyme cofactors/substrates, and the like. If desired the conjugate may further be attached to an affinity matrix using known techniques.

Examples of directly detectable labels that may be used with the conjugates include, but are not limited to, fluorescent moieties (such as fluorescent dyes including fluorescein and its derivatives, Texas red, rhodamine and its derivatives, dansyl, umbelliferone, or beads or microspheres containing fluorescent dyes), electron-dense moieties, chemiluminescent moieties (such as luciferin and 2,3-dihydrophthalazinediones, including luminol), magnetic particles, radiolabels (such as $^{3}H$, $^{125}I$, $^{35}S$, $^{14}C$, $^{32}P$ or $^{33}P$), nucleic acid intercalators (such as ethidium bromide, SYBR green), calorimetric labels (such as colloidal gold or coloured glass or plastic beads).

Signal detection can proceed by one of a variety of known methods, including spectroscopic, spectrophotometric, photochemical, biochemical, immunochemical, electrical, optical thermal, or chemical means, visual inspection, or other methods which track a molecule based upon colour, size, charge or affinity. Thus, for example, where the signal is due to a fluorescent moiety, detection can be by excitation of the fluorochrome with the appropriate wavelength of light and detection of the resulting fluorescence by, for example, microscopy, visual inspection, via photographic film, the use of electronic detectors such as digital cameras, charge coupled devices (CCDs) or photomultipliers and phototubes, and the like. Similar methods can be employed to detect luminescence, including scintillation counting. Where the signal is due to a radiolabel, means for detection include scintillation counters and autoradiography.

2.1 Compounds Capable of Inducing mRNA Degradation

Compounds that promote instability of mRNAs, which contain mRNA instability sequences can be identified using the assays of the present invention. Such compounds may be used to induce degradation of mRNAs, thus preventing or reversing inappropriate mRNA accumulation and thereby decreasing or preventing unwanted protein, e.g. cytokine, expression. Such compounds are potentially useful pharmaceutically for prophylaxis or treatment of diseases or medical conditions, which involve inappropriate mRNA stabilisation and accumulation and resultant undesirable protein expression.

The, instant invention, therefore, provides for compounds which destabilise mRNA, identifiable by a method of the present invention, or by use of a DNA expression system or an assay system according to the present invention.

3. Applications of the DNA Expression System 3.1 High-Throughput Analysis

One skilled in the art will appreciate that the techniques used in screening steps can be readily adapted for high-throughput analysis. High-throughput screens provide the advantage of processing a plurality samples simultaneously and significantly decrease the time required to screen a large number of samples. The present invention, therefore, contemplates the use of high-throughput methods for screening libraries of compounds to identify compounds that affect the stability of mRNA.

For high-throughput screening, reaction components are usually housed in a multi-container carrier or platform, such as a multi-well microtitre plate, which allows a plurality of reactions each containing a different test sample to be monitored simultaneously. The present invention also contemplates highly automated high-throughput screens to increase the efficiency of the screening process. Many high-throughput screening or assay systems are now available commercially, as are automation capabilities for many procedures such as sample and reagent pipetting, liquid dispensing, timed incubations, formatting samples into microarrays, microplate thermocycling and microplate readings in an appropriate detector, resulting in much faster throughput times.

3.2 Formulations/Kits

Formulations/kits containing the DNA expression system or assay of the present invention can be prepared by known techniques in the art. The present invention additionally provides for kits containing the reporter gene assay for use in identifying compounds that destabilise mRNA. The contents of the kit can be lyophilized and the kit can additionally contain a suitable solvent for reconstitution of the lyophilized components. Individual components of the kit would be packaged in separate containers and, associated with such containers, can be a list of instructions.

3.3 Pharmaceutical Compositions

Compounds identified by a method of the present invention, or by use of a DNA expression system or an assay system according to the present invention are potentially useful pharmaceuticals for prophylaxis or treatment of diseases or medical conditions, which involve inappropriate mRNA stabilisation and resultant undesirable protein expression/accumulation. The present invention, therefore, provides for pharmaceutical compositions comprising one or more of the identified compounds.

The pharmaceutical compositions and medicaments of the present invention may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. The pharmaceutically active compound or salts thereof may be present in association with one or more non-toxic pharmaceutically acceptable carriers and/or diluents and/or adjuvants and, if desired, other active ingredients.

The pharmaceutical compositions may be in a form suitable for oral use, for example, as tablets, troches, lozenges, aqueous or oily suspensions, dispersible powders or granules, emulsion hard or soft capsules, or syrups or elixirs. Compositions intended for oral use may be prepared according to methods known to the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed.

Pharmaceutical compositions for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Aqueous suspensions contain the active compound in admixture with suitable excipients including, for example, suspending agents, such as sodium carboxymethylcellulose, methyl cellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-deca-ethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavouring agents or one or more sweetening agents, such as sucrose or saccharin.

Oily suspensions may be formulated by suspending the active ingredients in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example, olive oil or arachis oil, or a mineral oil, for example, liquid paraffin, or it may be a mixtures of these oils. Suitable emulsifying agents may be naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents.

The pharmaceutical compositions may be in the form of a sterile injectable aqueous or oleaginous suspension. This suspension may be formulated according to known art using suitable dispersing or wetting agents and suspending agents such as those mentioned above. The sterile injectable preparation may also be sterile injectable solution or suspension in a non-toxic parentally acceptable diluent or solvent, for example, as a solution in 1,3-butanediol. Acceptable vehicles and solvents that may be employed include, but are not limited to, water, Ringer's solution, lactated Ringer's solution and isotonic sodium chloride solution. Other examples are, sterile, fixed oils which are conventionally employed as a solvent or suspending medium, and a variety of bland fixed oils including, for example, synthetic mono- or diglycerides. In addition, fatty acids such as oleic acid find use in the preparation of injectables.

Other pharmaceutical compositions and methods of preparing pharmaceutical compositions are known in the art and are described, for example, in "*Remington: The Science and Practice of Pharmacy*" (formerly "*Remington's Pharmaceutical Sciences*"); Gennaro, A., Lippincott, Williams & Wilkins, Philadelphia, Pa. (2000).

To gain a better understanding of the invention described herein, the following examples are set forth. It should be understood that these examples are for illustrative purposes only. Therefore, they should not limit the scope of this invention in any way.

EXAMPLES

Kastelic et al. (Cytokine, 1996, 8:751-761), previously demonstrated that radicicol analog A (the compound shown below) confers mRNA instability through the AU-rich element (ARE) motifs located in the 3' untranslated region (3' UTR) of genes subject to mRNA instability. For examples 1-5, the segment of 3' UTR of IL-1β which contains all the AREs was deleted and the resulting IL-1β-AU cDNA was subcloned into an expression vector. Stably transfected THP-1 cells containing this construct were analyzed by the RNase protection method (Kastelic et al. ibid.) and showed resistance of the AU-less derived RNA towards radicicol analog A.

The 3'UTR of IL-1β mRNA contains a total of 6 AUUUA motifs three of which are in tandem (see FIG. 1). For the construction of the luciferase reporter gene assay, we used only a fragment comprising the underlined sequence shown in FIG. 1 which contains three tandem repeats.

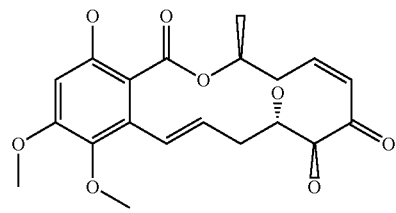

radicicol analogue A

Example 1

Construction of pGL2 Neo30 and Stable Cell Lines

Figure 3B:
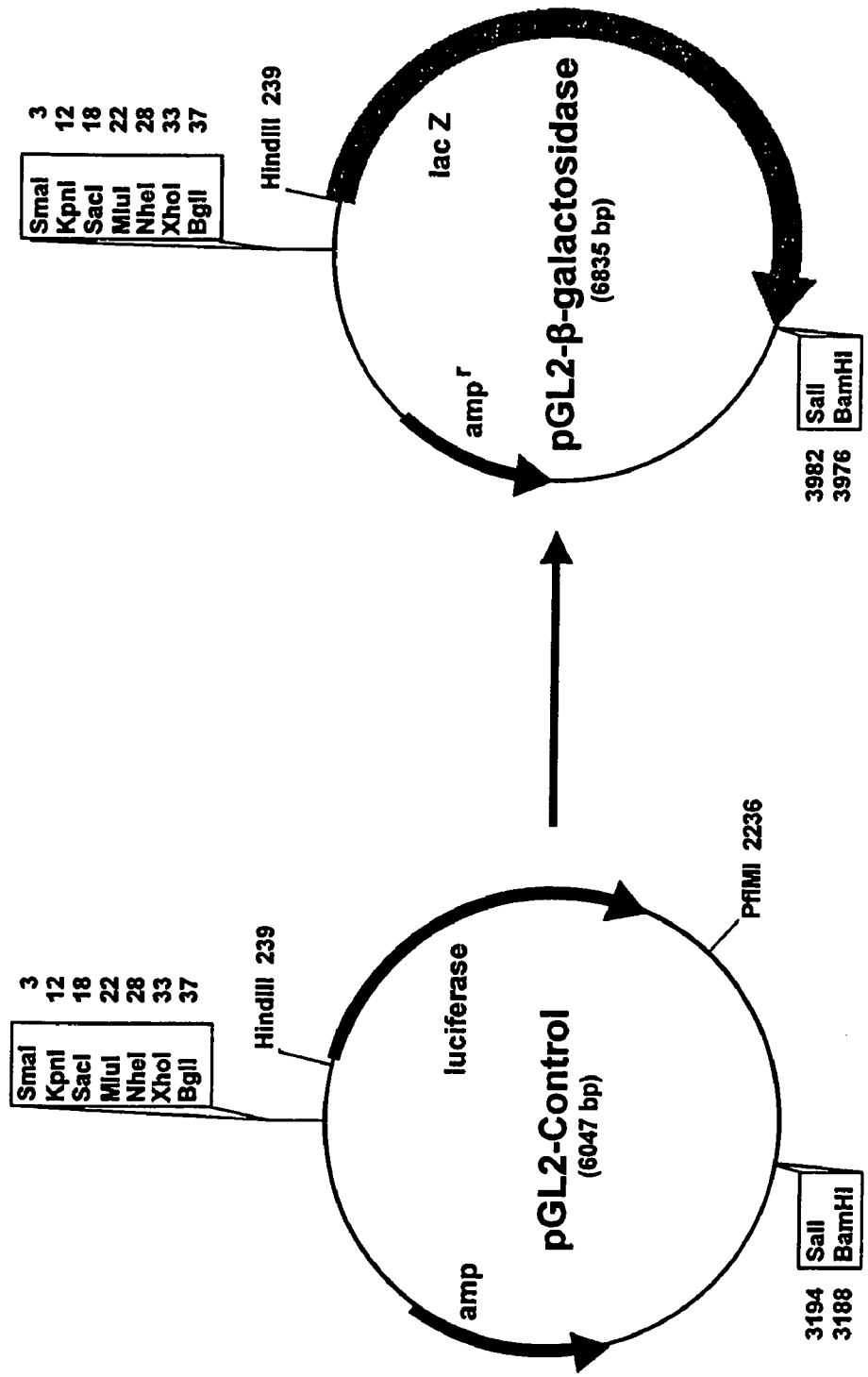
FIG. 3B shows plasmid diagram for pGL2-β-galactosidase.

In order to obtain a vector for stable integration into THP-1 cells, a XhoI-SalI fragment of the neo resistant gene (expressing aminoglycoside 3'phosphotransferase) derived from pMC1neoPolyA (Stratagene) was subcloned into the SalI site of pGL2-Control (Promega). This resulting plasmid was called pGL2_Neo. A 30 bp fragment (containing three tandem AUUUA motifs and flanking IL-1β 3'UTR sequence) obtained by annealing two complementary synthetic oligonucleotides (see FIG. 2) was subcloned into pGL2_Neo using the PflMI restriction site. This results in the luciferase expression vector pGL2_Neo30 (FIG. 3A). FIG. 2 shows the IL-1β3'UTR sequence containing three tandem AUUUA motifs used for ligation into the PflMI site of pGL2_Neo. Expression vector pGL2-β-galactosidase (FIG. 3B) has the lacZ gene driven by the same promoter (SV40) as the luciferase gene in pGL2_Neo30 and pGL2_Neo, but plasmid pGL2-β-galactosidase does not contain any mRNA instability sequences. The lacZ gene was obtained from a HindIII/BamHI restriction digest of pSV-beta-Galactosidase (Promega) and subcloned into the HindIII/BamHI site of pGL2-Control (Promega).

THP-1 cells were then cotransfected with either pGL2_Neo and pGL2-β-galactosidase vectors (to generate control cell lines) or with pGL2_Neo30 and pGL2-β-galactosidase vectors by electroporation. $10^7$ cells/ml in 1.3 mM $KH_2PO_4$, 7.36 mM $Na_2HPO_4$, 2.44 mM KCl, 124 mM NaCl, 5 mM glucose, 9.64 μM $MgCl_2$ and 16 μM $CaCl_2$ pH 7.2 were transfected with 20 μg of DNA in a Bio-Rad Gene Pulser (250V, 690 μF and indefinite resistance) using a 0.4 cm cuvette. Cells were subsequently cultured in RPMI medium containing 10% FBS, 2 mM L-Gln (L-glutamine), 50 μM 2-mercaptoethanol and 600 μg/ml of G418 (geneticin). After transfection of pGL2_Neo30 and pGL2_Neo into THP-1 cells, G418 resistant stable cell lines were obtained by selection with G418 and assayed for luciferase activity. Cotransfected cell lines were also assayed for β-galactosidase activity which can serve as an internal control (see Example 5 below). One cell line of each transfection was chosen for further analysis; the pGL2_Neo30/pGL2-β-galactosidase cell line was referred to as clone No. 63 and the pGL2_Neo/pGL2-β-galactosidase cell line as clone No. 53. No endogenous luciferase activity could be detected in normal THP-1 cells.

The tissue culture and luciferase activity measurements were carried out as described below.

Tissue Culture:

The transfected human monocytic leukaemia cell lines, clones No. 53 and 63 are grown in RPMI medium supplemented with 110 U/ml penicillin, 100 μg/ml streptomycin, 2 mM L-Gln and 2 g/l $NaHCO_3$. Heat-treated FBS (5%) is added before use. The cells are grown to a density of $5 \times 10^5$/ml and induced to differentiate with 100 U/ml (final concentration) γIFN. Three hours later, 10 μl of LPS (5 μg/ml final concentration) is added. This time point is designated time 0. Compounds are added at various times after LPS addition as indicated.

Luciferase Activity Measurement:

In order to adapt the system to the use of 96 well plates, cells were grown in Packard flat bottom white polystyrene microplates (Cat. No. 6005180) in RPMI medium lacking phenol red (AMIMED). Cells were plated at $5 \times 10^4$/well. After treatment of the cells, luciferase was measured using the Packard Luc Lite system (Cat. No. 601691 1) according to the manufacturer's instructions in a final volume of 205 μl. Briefly, to a cell suspension of $5 \times 10^5$ cells/ml, γIFN (1000 U/ml, Boehringer Mannheim, No. 1050494) to a final concentration of 100 U/ml and 0.25% (v/v) Luc Lite Enhancer was added. After a 3 hour incubation LPS (50 μg/ml Sigma, L-8274) was added to give 5 μg/ml final concentration. The cells were then plated at $5 \times 10^4$/100 μl/well into flat bottom white polystyrene microplates (Packard, Cat. No. 6005180) and incubated for 16 hours. 5 μl of compound solution or control vehicle was then added and the cells were further incubated as indicated. 100 μl of luciferase substrate solution was added and the plates were covered with TopSeal-A press-on adhesive sealing film (Packard Cat. No. 6005185) before measuring luminescence with a Packard Top Count Scintillation Counter at 22° C. The luciferase signal was stable for at least 90 min.

Figure 4:
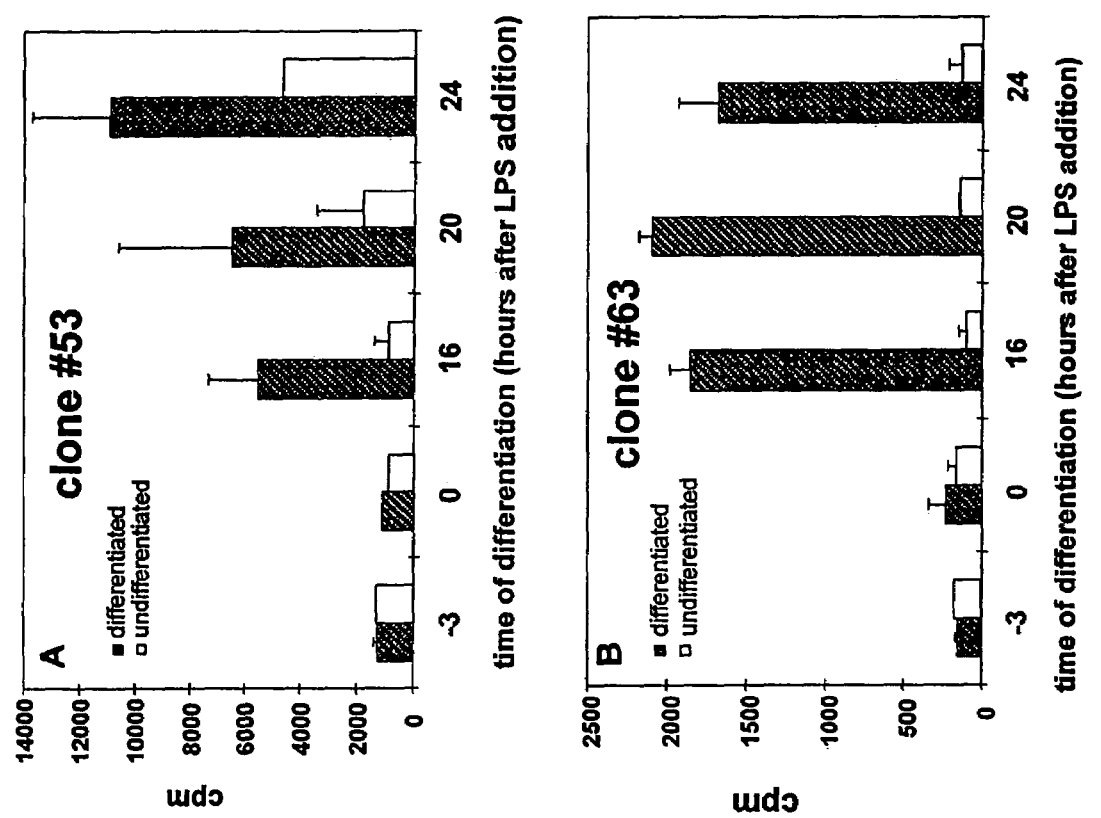
FIG. 4 shows graphs of luciferase activity over the time of differentiation for clone No. 53 (A) and clone No. 63 (B)

The differentiation-dependent induction of luciferase activity in the two cell lines, Nos. 53 (A) and 63 (B) were tested and the results obtained are shown in FIGS. 4A and B.

In both clones a distinct induction of luciferase expression was observed, maintaining high levels of activity throughout the time of the assay. This elevated and constant expression of luciferase should be born in mind when analyzing effects of compounds inducing mRNA instability. mRNA degradation will be in constant competition with de novo transcription, unlike the situation in wild-type THP-1 cells where in the case of IL-1β mRNA, highest levels were obtained 16 hours after LPS addition. One would expect in the case of luciferase to see a weaker effect of mRNA destabilizing drugs since transcription remains high, as was observed in the case of radicicol analog A, see below.

Example 2

Half Life of Luciferase mRNA and Protein

Figure 5:
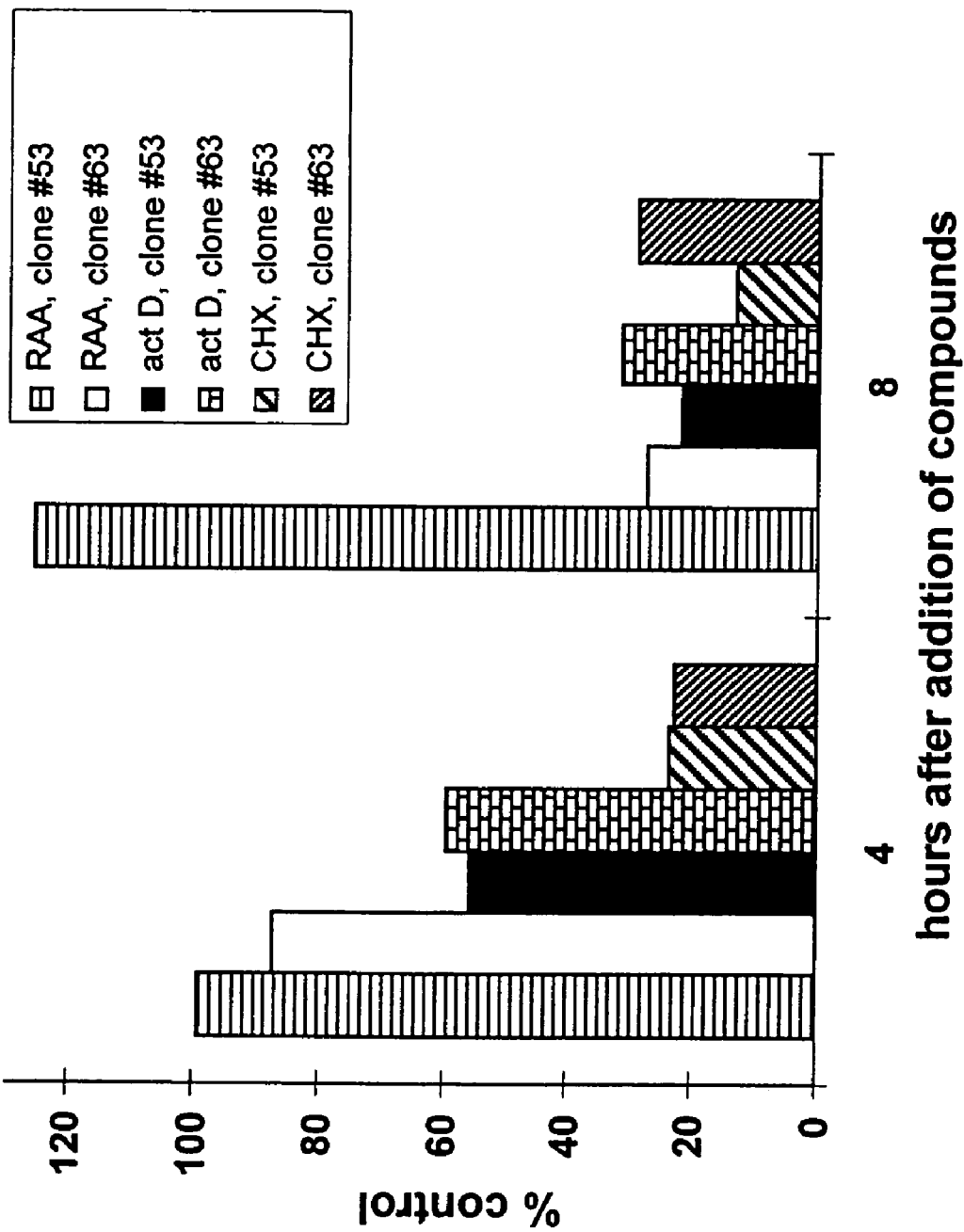
FIG. 5 shows graphs of luciferase half lives, 4 and 8 hours after addition of compounds for clones No. 53 and 63 treated with radicicol analog A (RAA), actinomycin D (act D.) and cyclohexamide (CHX)

To measure mRNA degradation using luciferase protein activity it is important to know the half life of the luciferase enzyme in order to determine an optimal time for assaying for potential mRNA destabilizing agents by way of luciferase protein stability. The possibility exists that mRNA could be degraded but due to a long half life of the protein, high enzyme activities could persist. Therefore we analyzed luciferase activities after addition of the transcriptional inhibitor actinomycin D (act. D) or the translational inhibitor cycloheximide (CHX). FIG. 5 shows that in the presence of 20 μg/ml act. D as well as in the presence of 20 μM CHX, luciferase activities rapidly declined and after 8 hours of incubation reached a level comparable to the inhibition achieved by radicicol analog A (1 μM). In view of this relatively short half life of the luciferase enzyme, it is safe to assess substances for activity on mRNA degradation as early as 8 hours after compound addition.

Example 3

Effect of the Radicicol Analog A

Figure 6:
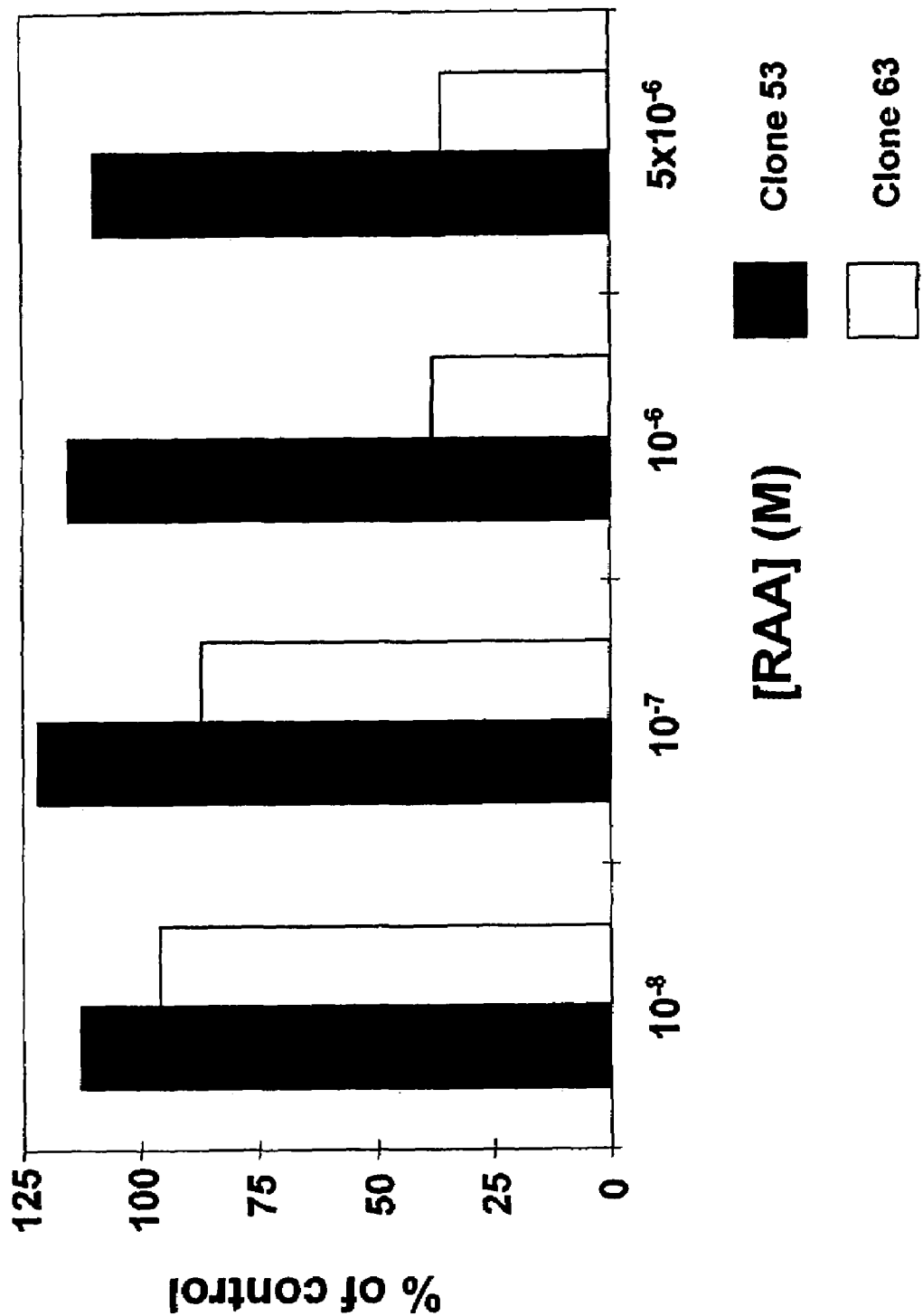
FIG. 6 shows graphs of luciferase activity from clones No. 53 (solid bars) and 63 (open bars) treated with various concentrations of radicicol analog A (RAA)

The THP-1 cell lines, clone Nos. 63 and 53 are grown, differentiated with γIFN and stimulated with LPS identical to normal THP-1 cells. Radicicol analog A was added 16 hours after the addition of LPS and cell extracts were then taken 8 hours later or as indicated. Luciferase activity was inhibited by 1 μM radicicol analog A on average by 50%+/−17%, in some cases inhibition was as great as 93%, whereas up to $5 \times 10^{-6}$ M of radicicol analog A had no effects on the control clone No. 53, FIG. 6 (solid bars indicate clone No. 53, open bars clone No. 63).

Figure 7:
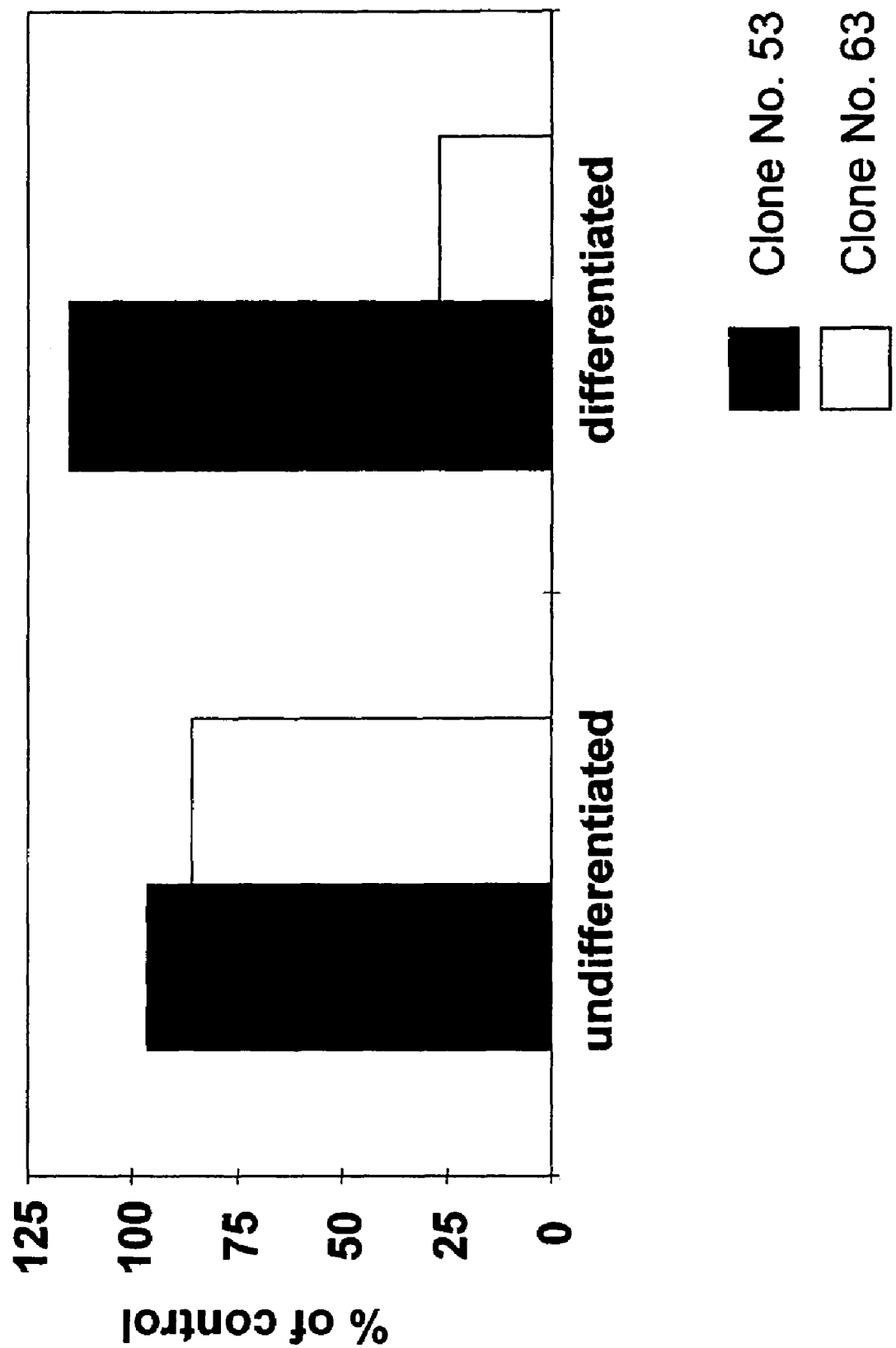
FIG. 7 shows graphs of luciferase activity for undifferentiated and differentiated clone No. 53 (solid bars) and clone No. 63 (open bars) with an 8 hr. treatment of 1 μM radicicol analog A (RAA)

Interestingly, undifferentiated clone No. 63 (open bars) when treated with 1 μM radicicol analog A showed only a limited reduction of luciferase activity (FIG. 7, solid bars indicate clone No. 53), which is either due to the lower expression of luciferase or is indicative of the involvement of a differentially expressed or modified component in the mRNA degradation process mediated by AU-rich elements. Indeed, gel retardation experiments using 241 bp of the AU-rich 3' UTR of IL-1β as a riboprobe showed the binding of additional proteins with γIFN induced differentiation or modification (not shown).

Figure 8:
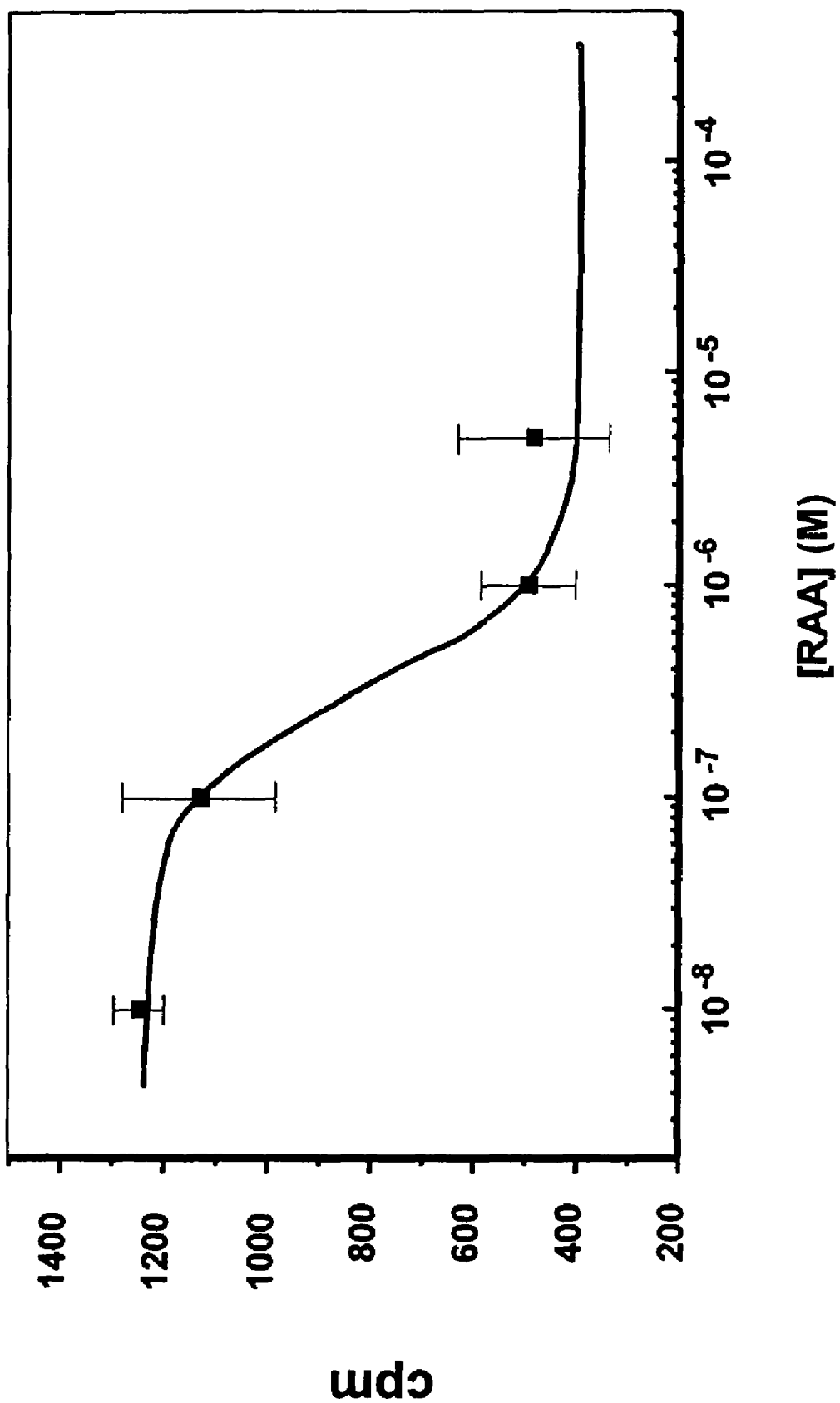
FIG. 8 shows a graph of the concentration dependent inhibition of luciferase activity in differentiated clone No. 63 after an 8 hr. treatment with radicicol analog A (RAA)

Concentration dependent inhibition of luciferase activity in differentiated clone No. 63, is shown in FIG. 8. Concentrations of radicicol analog A higher than $5 \times 10^{-6}$ M also inhibited the control clone (No. 53) due to cytotoxicity or inhibitory activity on transcription.

Example 4

Application of Assay to a Number of Selected Substances

A number of selected substances were tested for their activity in the assay of the invention substantially as described in Example 3 (for differentiated cells). The results obtained are given in Table 3 below. Radicicol (see formula II below) and radicicol analog A showed a clear effect on mRNA stability; other compounds tested did not show activity in the assay used.

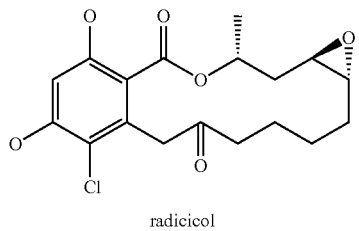

radicicol

II

TABLE 3

Testing the mRNA stability in two separate cell lines in the presence of selected compounds

| Compound | Luciferase Activity (% of Control) | |
|---|---|---|
| (1 µM) | Clone No. 53 | Clone No. 63 |
| Peptidic ICE inhibitor | 87 | 104 |
| Stemphon | 95 | 90 |
| Radicicol | 98 | 47 |
| (17α)-23-(E)-dammara-20,23-dien-3β,25-diol | 116 | 91 |
| Radicicol analog A | 120 | 49 |
| Thalidomide | 98 | 112 |
| Dexamethasone | 72 | 63 |
| Cyclosporin A | 82 | 74 |

Example 5

Application of Assay Using a Single Cell Line

In the previous examples, test compounds were assayed by comparing their activity in two separate cell lines (clone Nos. 53 and 63). However, clone 63 was cotransfected with two separate plasmids: one plasmid (pGL2_Neo30) contained the luciferase gene with the 30 bp instability sequence driven by the SV40 promoter and the other plasmid (pGL2-β-galactosidase, FIG. 3B) contained the lacZ gene driven by the SV40 promoter but contained no mRNA instability sequences. The β-galactosidase activity of this cell line should not be affected by exposure of the cells to compounds which promote mRNA instability via mRNA instability sequences. As a result, one should be able to screen for compounds having mRNA instability activity by simply comparing luciferase activity in unstimulated cells versus stimulated cells and comparing the β-galactosidase activity in these same cells. Therefore, the effect of radicicol analog A on luciferase activity and β-galactosidase activity in clone 63 (stimulated and unstimulated cells) was compared to the effect of radicicol analog A on stimulated and unstimulated cells of clone 63 and clone 53. The assay was performed as described in the previous Examples. Table 4 shows the luciferase activities of various concentrations of radicicol analog A in γIFN/LPS stimulated and unstimulated cells of clones 63 and 53. Activities are given in % of control and were based on means of three independent experiments controlled for cell numbers. Table 5 shows the β-galactosidase activities in stimulated and unstimulated cells of clone 63 and 53. Activities are given in % of control and were based on means of three independent experiments controlled for cell numbers. It is clear from the data that both the assay of Table 4 and that of Table 5 would have identified radicicol analog A as an active compound.

TABLE 4

Luciferase activities of various concentrations of radicicol analog A in γIFN/LPS stimulated and unstimulated cells of clones 63 and 53

| | Luciferase Activity | | | |
|---|---|---|---|---|
| | Clone 63 | | Clone 53 | |
| Compound | Unstimulated (% control) | γIFN/LPS stimulated (% control) | Unstimulated (% control) | γIFN/LPS stimulated (% control) |
| none | 100 | 100 | 100 | 100 |
| 1 µM RAA | 63 | 7 | n.d. | 88 |
| 10 µM RAA | 11 | 2 | 87 | 63 |

TABLE 5

β-galactosidase activities in stimulated and unstimulated cells of clone 63 and 53

| | β-galactosidase activity | | | |
|---|---|---|---|---|
| | Clone 63 | | Clone 53 | |
| Compound | Unstimulated (% control) | γIFN/LPS stimulated (% control) | Unstimulated (% control) | γIFN/LPS stimulated (% control) |
| none | 100 | 100 | 100 | 100 |
| 1 µM RAA | 96 | 97 | 99 | 98 |
| 10 µM RAA | 84 | 70 | 103 | 62 |

Example 6

Construction of pGL2NeoN/N Luciferase Expression Vector

Plasmid pGL2_Neo (Promega) was modified as follows to include additional restriction enzyme sites in order to facilitate cloning of various instability sequences as outlined in Examples 7-14 (below).

Two unphosphorylated oligonucleotides, N/N-TK5P: TGCGGCCGCAA<u>CATATG</u>TTCCT (SEQ ID NO: 31) and N/N-TK3P: AA<u>CATATG</u>TTGCGGCCGCAAGG (SEQ ID NO: 32) were annealed and ligated into PflM1 linearized pGL2_Neo. The annealed oligonucleotides formed a small multiple cloning site containing the restriction enzyme sites for NotI (shown in bold and italics) and NdeI (shown in bold, italics and underline). It should be noted that this small multiple cloning site can be enlarged to contain additional unique restriction sites. The orientation of the NotI/NdeI multiple cloning site of the resulting plasmid, pGL2NeoN/N, was verified by DNA sequencing.

Example 7

Construction of Human APP Instability Sequence

The APP sequence used in this example was derived from human mRNA for amyloid A4 precursor corresponding to Alzheimer's disease (GenBank accession number: Y00264, locus: HSAFPA4). The 3' UTR of the amyloid A4 precursor sequence contains 5 AUUUA motifs. A human multiple tissue cDNA (Clontech, MTC Panel I, K1420-1, source: brain) was PCR amplified using a 3' primer, TK-APP-3P, a 5' primer, TK-APP-5P and Platinum Pfx DNA polymerase (Invitrogen).

TK-APP-3P: TTGCGGCCGCTACATGAAAACAC-CATTTTATAC, SEQ ID NO:9, contains additional 5' sequence including a NotI restriction site. Shown in bold is the sequence identical to the human APP sequence from 3309 to 3331. Potential polyA signal sequences are located at 3081 . . . 3086 and 3090 . . . 3095.

TK-APP-5P: TGCGGCCGCCACAGCAGCCTCT-GAAGTTGG, SEQ ID NO:10, contains additional 5' sequence including a NotI restriction site. Shown in bold is the sequence identical to the human APP sequence from 2240 to 2264.

The resulting DNA fragment is shown in FIG. 9 (SEQ ID NO:1) and represents 1093 nucleotides of the 3' UTR of the human amyloid A4 precursor protein gene from position 2240 (the stop codon is located at 2235) up to, and including, position 3331, which is just upstream of the third putative polyA signal sequence (3332 . . . 3337). The fragment contains 5 AUUUA motifs. This fragment was blunt-end cloned into pCR-Blunt II-TOPO (Invitrogen) which was used as a shuttle vector. A NotI fragment was digested out of the shuttle vector and subcloned into NotI linearized pGL2NeoN/N luciferase expression vector. The resulting DNA expression vector comprises the 3'UTR of the human amyloid A4 precursor protein gene, containing 5 AUUUA motifs, inserted into the 3'UTR of the luciferase gene used in pGL2NeoN/N.

Example 8

Construction of Human bcl-2α Long Instability Sequence

The bcl-2-alpha sequence used in this example was derived from human mRNA for B-cell 2 (bcl-2) proto-oncogene corresponding to leukaemia/lymphoma disease (GenBank accession number: M13994, locus: HUMBCL2A). The 3' UTR of the bcl-2-alpha sequence contains 8 AUUUA motifs, 3 of which are in tandem. Total RNA from human HL-60 cells (acute promyelocytic leukaemia) was reverse transcribed using a 3' primer, hbcl2a-TK3PL and SuperScript II RNase H⁻ reverse transcriptase (Invitrogen). The resulting first-strand synthesised cDNA was then PCR amplified using the 3' primer, hbcl2a-TK3PL, a 5' primer, hbcl2a-TK5P, and Platinum Pfx DNA polymerase (Invitrogen).

hbcl2a-TK3PL: AGCGGCCGCACTTCCTCAAGTTC-CAGAGG, SEQ ID NO:11, contains additional 5' sequence including a NotI restriction site. Shown in bold is the sequence identical to the human bcl-2-alpha sequence from 3041 to 3061. The 3'UTR of this mRNA is extremely long and extends to position 5086.

hbcl2a-TK5P: AGCGGCCGCTGAAGTCAACATGCCT-GCC, SEQ ID NO:12, contains additional 5' sequence including a NotI restriction site. Shown in bold is the sequence identical to the human bcl-2-alpha sequence from 2176 to 2194. The stop codon is located at position 2176.

Figure 10:
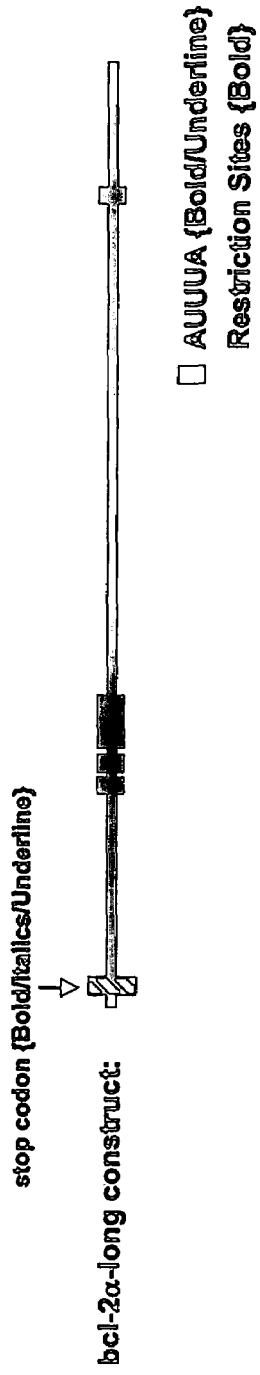
FIG. 10 shows the cDNA construct derived from the Human bcl-2α long 3'UTR (SEQ ID NO:2)

The resulting DNA fragment is shown in FIG. 10 (SEQ ID NO:2) and represents 889 nucleotides of the 3' UTR of the bcl-2-alpha protein gene from position 2176 (the stop codon is located at 2176) up to, and including, position 3061. The fragment contains 6 AUUUA motifs. This fragment was amplified with the Expand High Fidelity PCR System (Roche). The product, which has 3' A overhangs, was cloned into pCR-XL-TOPO (Invitrogen) and used as a shuttle vector. A NotI fragment was digested out of the shuttle vector and subcloned into NotI linearized pGL2NeoN/N luciferase expression vector. The resulting DNA expression vector comprises the 3'UTR of the human bcl-2-alpha protein gene containing the first 6 AUUUA motifs inserted into the 3'UTR of the luciferase gene used in pGL2NeoN/N.

Example 9

Construction of Human bcl-2 α Short Instability Sequence

The bcl-2-alpha sequence used in this example was derived from human mRNA for B-cell 2 (bcl-2) proto-oncogene corresponding to leukaemia/lymphoma disease (GenBank accession number: M13994, locus: HUMBCL2A). The 3' UTR of the bcl-2-alpha sequence contains 8 AUUUA motifs, 3 of which are in tandem. Total RNA from human HL-60 cells (acute promyelocytic leukaemia) was reverse transcribed using a 3' primer, hbcl2a-TK3PS and SuperScript II RNase H⁻ reverse transcriptase (Invitrogen). The resulting first-strand synthesised cDNA was then PCR amplified using the 3' primer, hbcl2a-TK3PS, a 5' primer, hbcl2a-TK5P, and Platinum Pfx DNA polymerase (Invitrogen).

hbcl2a-TK3PS: AGCGGCCGCATTTTTCCCATCGCT-GTCC, SEQ ID NO:13, contains additional 5' sequence including a NotI restriction site. Shown in bold is the sequence identical to the human bcl-2-alpha sequence from 2848 to 2878. The 3'UTR of this mRNA is extremely long and extends to position 5086.

hbcl2a-TK5P: AGCGGCCGCTGAAGTCAACATGCCT-GCC, SEQ ID NO:12, contains additional 5' sequence including a NotI restriction site. Shown in bold is the sequence identical to the human bcl-2-alpha sequence from 2176 to 2194. The stop codon is located at position 2176.

Figure 11:
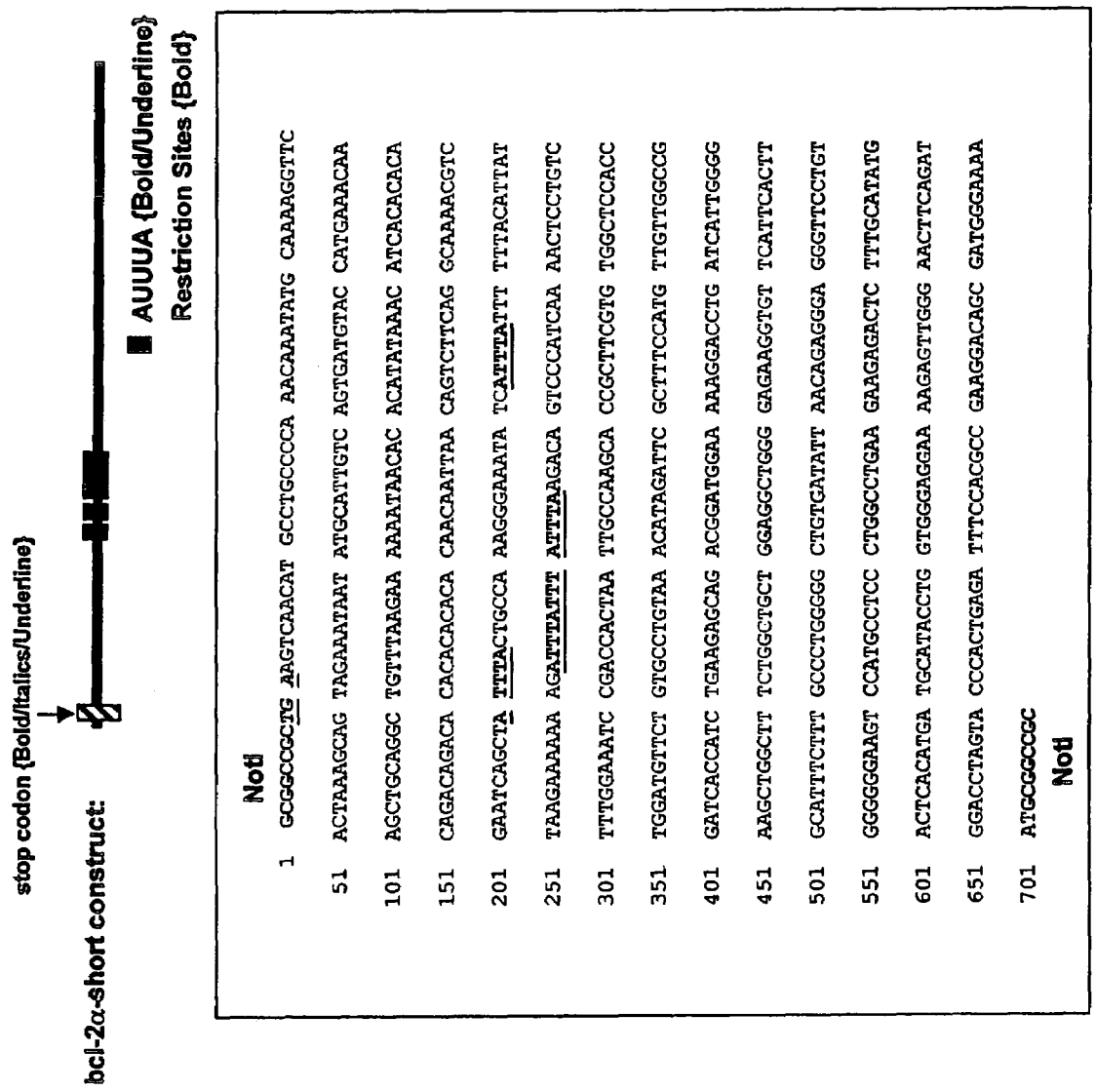
FIG. 11 shows the cDNA construct derived from the Human bcl-2α short 3'UTR (SEQ ID NO:3)

The resulting DNA fragment is shown in FIG. 11 (SEQ ID NO:3) and represents 696 nucleotides of the 3' UTR of the bcl-2-alpha protein gene from position 2176 (the stop codon is located at 2176) up to, and including, position 2878. The fragment contains 5 AUUUA motifs. This fragment was amplified with the Expand High Fidelity PCR System (Roche). The product, which has 3' A overhangs, was cloned into pCR-XL-TOPO (Invitrogen) and used as a shuttle vector. A NotI fragment was digested out of the shuttle vector and subcloned into NotI linearized pGL2NeoN/N luciferase expression vector. The resulting DNA expression vector comprises the 3'UTR of the human bcl-2-alpha protein gene containing the first 5 AUUUA motifs inserted into the 3'UTR of the luciferase gene used in pGL2NeoN/N.

Example 10

Construction of Human c-myc Instability Sequence

The c-myc sequence used in this example was derived from human c-myc gene for p67 and p64 myc proteins (GenBank accession numbers: D10493 and D90467, locus: HUMMY-CKOB). The genomic organization of the human c-myc shows that p67 and p64 have a common 3'UTR containing 4, isolated AUUUA sequences. The terminal exon of both proteins (nucleotides 6628-7190) contain the 60 amino acid domain known as the coding region instability determinant (crd) described by Bernstein et al. (Genes and Dev., 1992, 6, 642-652) from 7008 to the stop codon (7190). Total RNA from human HL-60 cells (acute promyelocytic leukaemia) was reverse transcribed using a 3' primer, hcmyc-TK3P and SuperScript II RNase H⁻ reverse transcriptase (Invitrogen). The resulting first-strand synthesised cDNA was then PCR amplified using the 3' primer, hcmyc-TK3P, a 5' primer, hcmyc-TK5P, and Platinum Pfx DNA polymerase (Invitrogen).

hcmyc-TK3P: CCATATGGCTCAATGATATATTTGC-CAG, SEQ ID NO:14, contains additional 5' sequence including a NdeI restriction site. Shown in bold is the sequence identical to the human c-myc sequence from 7636 to 7658. Two polyA signal sequences are located at 7485 . . . 7490 and 7626 . . . 7631.

hcmyc-TK5P: AGCGGCCGCTCGGAGCTTTTTTGC-CCTGCGTG, SEQ ID NO:15, contains additional 5' sequence including a NotI restriction site. Shown in bold is the sequence identical to the cmyc sequence from 6984 to 7005.

Figure 12:
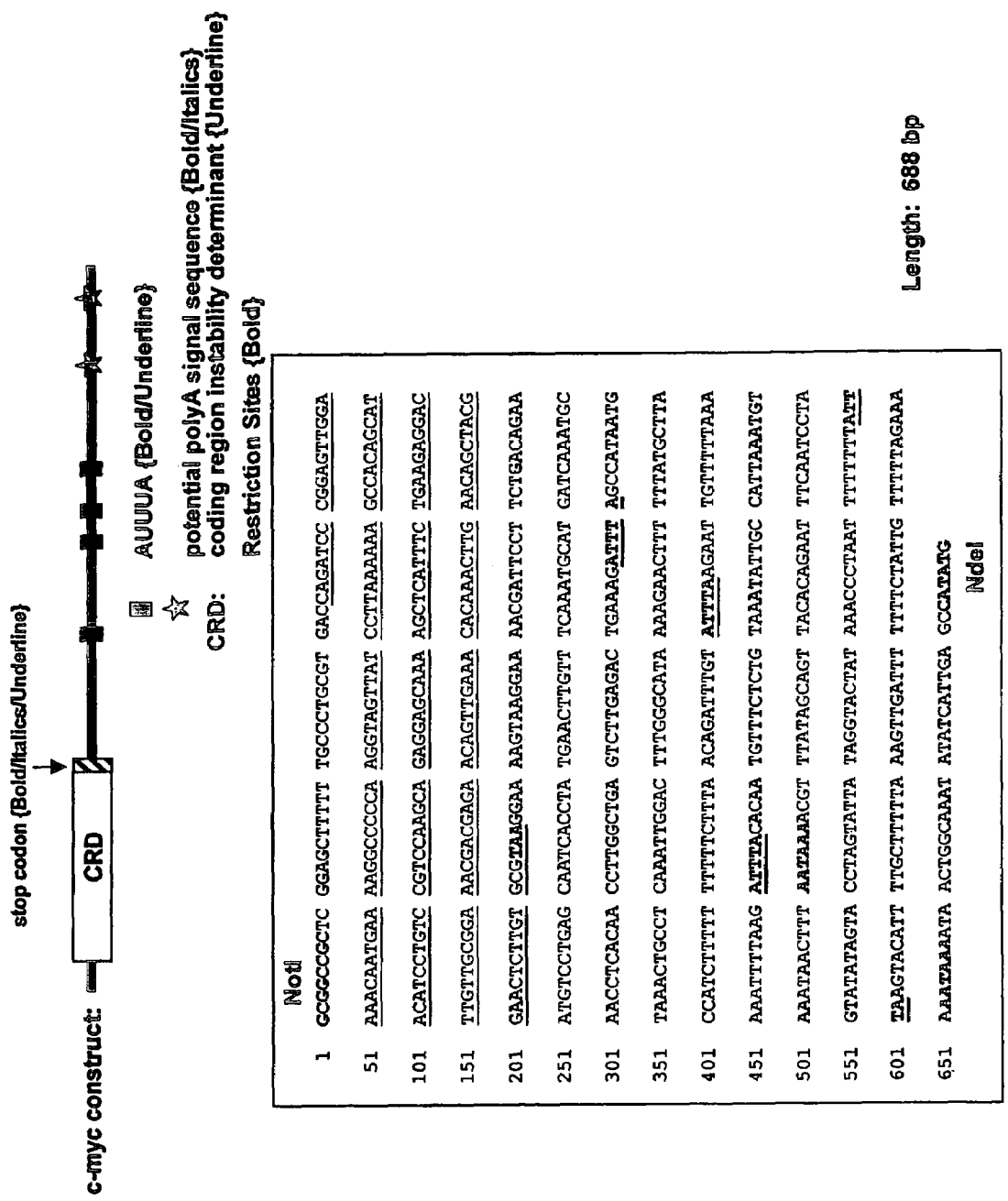
FIG. 12 shows the cDNA construct derived from the Human c-myc 3'UTR (SEQ ID NO:4)

The resulting DNA fragment is shown in FIG. 12 (SEQ ID NO:4) and represents 675 nucleotides of the 3' UTR of the human c-myc protein gene from position 6984 up to, and including, position 7658. The fragment contains 4 AUUUA motifs. The fragment was amplified with the Expand High Fidelity PCR System (Roche). The product, which has 3' A overhangs, was cloned into pCR-XL-TOPO (Invitrogen) and used as a shuttle vector. The NotI/NdeI fragment was digested out of the shuttle vector and subcloned into NotI/NdeI linearized pGL2NeoN/N luciferase expression vector. The resulting DNA expression vector comprises the 3'UTR of the human c-myc protein gene containing 4 AUUUA motifs inserted into the 3'UTR of the luciferase gene used in pGL2NeoN/N.

Example 11

Construction of Human TNFα Instability Sequence

The TNFα mRNA sequence used in this example was derived from human tumor necrosis factor (TNF superfamily, member 2) (TNF) mRNA (GenBank accession number: NM_000594, locus: TNF). The 3' UTR of this mRNA has 9 AUUUA motifs. Total RNA from human THP-1 cells (differentiated with γIFN/LPS) was isolated and reverse transcribed using a 3' primer, TKHT3P and SuperScript II RNase H⁻ reverse transcriptase (Invitrogen). The resulting first-strand synthesised cDNA was then PCR amplified using the 3' primer, TKHT3P, a 5' primer, TKHT5P, and Platinum Pfx DNA polymerase (Invitrogen).

TKHT3P: CCATATGAAGCAAACTTTATTTCTCGCC, SEQ ID NO:16, contains additional 5' sequence including a NdeI restriction site. Shown in bold is the sequence identical to the human TNFα sequence from 1640 to 1660. A potential polyA signal sequence is located at 1647 . . . 1652. Addition of the polyA tail occurs at 1666 or 1669.

TKHT5P: AGCGGCCGCTGAGGAGGACGAACATC-CAACC, SEQ ID NO:17, contains additional 5' sequence including a NotI restriction site. Shown in bold is the sequence identical to the human TNFα sequence from 869 to 890.

The resulting DNA fragment is shown in FIG. 13 (SEQ ID NO:5) and represents 792 nucleotides of the 3' UTR of the human TNFα protein gene from position 869 up to, and including, position 1660. The fragment contains 9 AUUUA motifs. The fragment was blunt-end cloned into pCR-Blunt II-TOPO (Invitrogen) which was used as a shuttle vector. The NotI/NdeI fragment was digested out of the shuttle vector and subcloned into NotI/NdeI linearized pGL2NeoN/N luciferase expression vector. The resulting DNA expression vector comprises the 3'UTR of the human TNFα protein gene containing 9 AUUUA motifs inserted into the 3'UTR of the luciferase gene used in pGL2NeoN/N.

Example 12

Construction of Human IL-1β Instability Sequence

The IL-1β mRNA sequence used in this example was derived from the human gene for prointerleukin 1 beta (GenBank accession number: X04500, locus: HSIL1B). The 3' UTR of this mRNA has 6 AUUUA motifs. Total RNA from human THP-1 cells (differentiated with γIFN/LPS) was isolated and reverse transcribed using a 3' primer, HIL1B3 and SuperScript II RNase H⁻ reverse transcriptase (Invitrogen). The resulting first-strand synthesised cDNA was then PCR amplified using the 3' primer, HIL1B3, a 5' primer, HIL1B5, and Platinum Pfx DNA polymerase (Invitrogen).

HIL1B3: CCATATGGTGAAGTTTATTTCAGAACC, SEQ ID NO:18, contains additional 5' sequence including a NdeI restriction site. Shown in bold is the sequence identical to the human IL-1β sequence from 8917 to 8936. A potential polyA signal sequence is located at 8925 . . . 8930.

HIL1B5: AGCGGCCGCTAAAGAGAGCTGTACCCA-GAG, SEQ ID NO:19, contains additional 5' sequence including a NotI restriction site. Shown in bold is the sequence identical to the human IL-1β sequence from 8337 to 8357.

Figure 14:
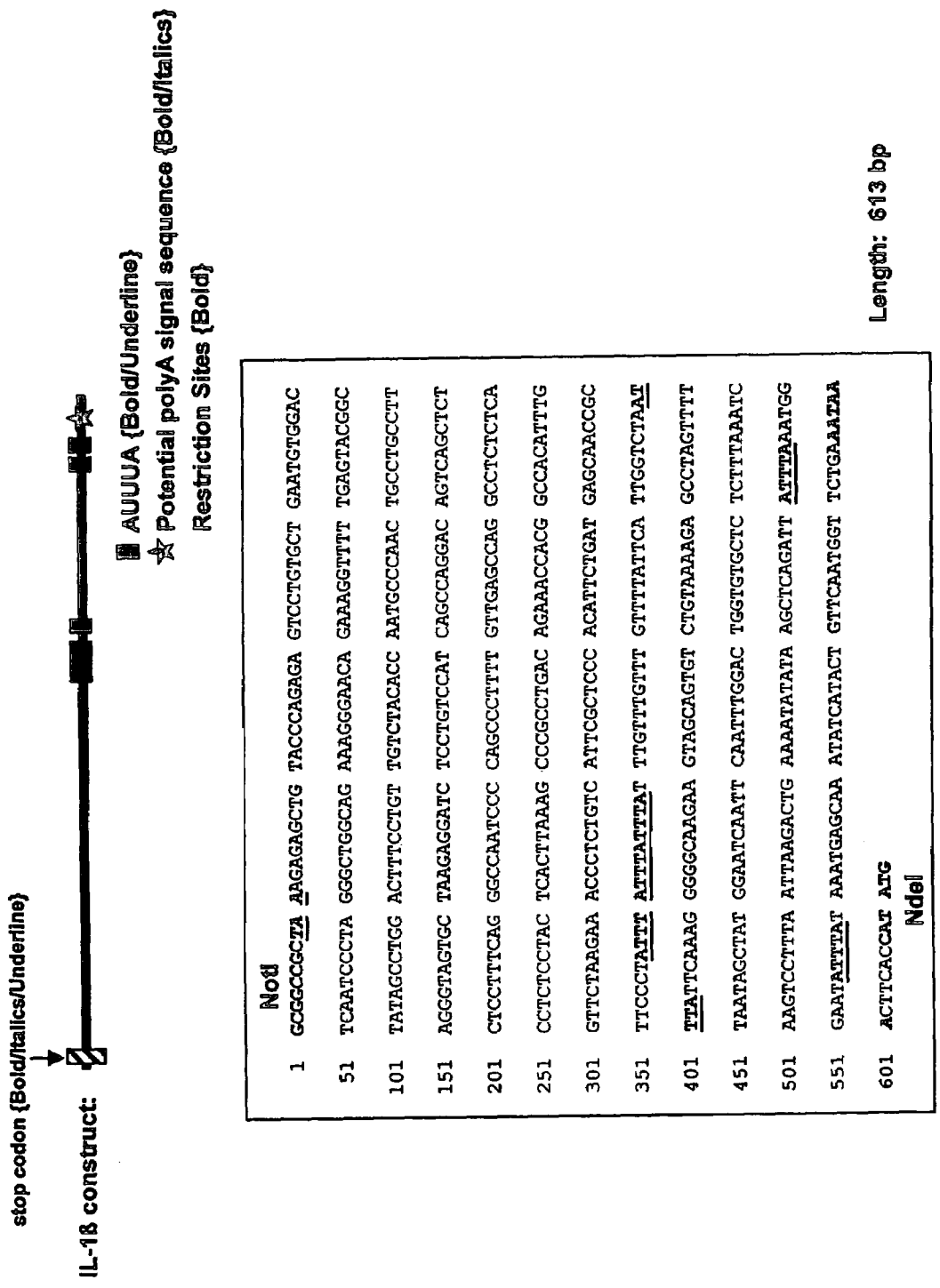
FIG. 14 shows the cDNA construct derived from the Human IL-1β 3'UTR (SEQ ID NO:6)

The resulting DNA fragment is shown in FIG. 14 (SEQ ID NO:6) and represents 600 nucleotides of the 3' UTR of the human IL-1β protein gene from position 8337 up to, and including, position 8936. The fragment contains 6 AUUUA motifs. The fragment was blunt-end cloned into pCR-Blunt II-TOPO (Invitrogen) which was used as a shuttle vector. The NotI/NdeI fragment was digested out of the shuttle vector and subcloned into NotI/NdeI linearized pGL2NeoN/N luciferase expression vector. The resulting DNA expression vector comprises the 3' UTR of the human IL-1β protein gene containing 6 AUUUA motifs inserted into the 3'UTR of the luciferase gene used in pGL2NeoN/N.

Example 13

Construction of Human VEGF Instability Sequence

The vascular endothelial growth factor (VEGF) mRNA sequence used in this example was derived from the human gene for VEGF (GenBank accession number: AF022375). The 3' UTR of this mRNA has 8 AUUUA motifs, all present in single copies. VEGF mRNA also has a reported hypoxia-induced mRNA stability region located in the 3'UTR (Claffey et al., 1998, Mol. Biol. Cell 9:469-481). A human multiple tissue cDNA (Clontech, MTC Panel I, K1420-1, source: placenta) was PCR amplified using a 3' primer, TK-VAU-3P, a 5' primer, TK-VAU-5P and Platinum Pfx DNA polymerase (Invitrogen).

TK-VAU-3P: AACATATGTTCTGTATTTCTTTGTCGT-TGTTT, SEQ ID NO:20, contains additional 5' sequence including a NdeI restriction site. Shown in bold is sequence identical to the VEGF sequence from 3124 to 3146. The 3'UTR of this mRNA is extremely long and extends to position 3166. There appears to be a polyA tail starting at position 3155 and what may be a potential polyA addition sequence at 3139 . . . 3144.

TK-VAU-5P: TGCGGCCGCATTGCTGTGCTTTGGG-GATTCCC, SEQ ID NO:21, contains additional 5' sequence including a NotI restriction site. Shown in bold is the sequence identical to the VEGF sequence from 2062 to 2085. The stop codon is located at position 1275.

The resulting DNA fragment is shown in FIG. 15 (SEQ ID NO:7) and represents 1087 nucleotides of the 3' UTR of the human VEGF protein gene from position 2062 (the stop codon is located at 1275) up to, and including, position 3146. The fragment contains 7 AUUUA motifs. The fragment was blunt-end cloned into pCR-Blunt II-TOPO (Invitrogen) which was used as a shuttle vector. A NotI/NdeI fragment was digested out of the shuttle vector and subcloned into NotI/NdeI linearized pGL2NeoN/N luciferase expression vector. The resulting DNA expression vector comprises the 3'UTR of the human VEGF protein gene containing 7 AUUUA motifs inserted into the 3'UTR of the luciferase gene used in pGL2NeoN/N.

Example 14

Construction of Human VEGF Hypoxia Domain Instability Sequence

The vascular endothelial growth factor (VEGF) mRNA sequence used in this example was derived from the human gene for VEGF (GenBank accession number: AF022375). The 3' UTR of this mRNA has 8 AUUUA motifs, all present in single copies. VEGF mRNA also has a reported hypoxia-induced mRNA stability region located in the 3'UTR (Claffey et al., 1998, Mol. Biol. Cell 9:469-481). A human multiple tissue cDNA (Clontech, MTC Panel I, K1420-1, source: placenta) was PCR amplified using a 3' primer, TK-V-3P, a 5' primer, TK-V-5P and Platinum Pfx DNA polymerase (Invitrogen).

TK-V-3P: AACATATGTTCATCCAGTGAAGACAC-CAATAAC, SEQ ID NO:22, contains additional 5' sequence including a NdeI restriction site. Shown in bold is sequence identical to the VEGF sequence from 1730 to 1752. The 3'UTR of this mRNA is extremely long and extends to position 3166. There appears to be a polyA tail starting at position 3155 and what may be a potential polyA addition sequence at 3139 . . . 3144.

TK-V-5P: TGCGGCCGCATTCCTGTAGACACAC-CCACCC, SEQ ID NO:23, contains additional 5' sequence including a NotI restriction site. Shown in bold is the sequence identical to the VEGF sequence from 1601 to 1622. The stop codon is located at position 1275.

Figure 16:
FIG. 16 shows the cDNA construct derived from the Human VEGF hypoxia domain 3'UTR (SEQ ID NO:8)

The resulting DNA fragment is shown in FIG. 16 (SEQ ID NO:8) and represents 152 nucleotides of the 3' UTR of the human VEGF protein gene from position 1601 (the stop codon is located at 1275) up to, and including, position 1752. The fragment contains the reported hypoxia domain. The fragment was blunt-end cloned into pCR-Blunt II-TOPO (Invitrogen) which was used as a shuttle vector. A NotI/NdeI fragment was digested out of the shuttle vector and subcloned into NotI/NdeI linearized pGL2NeoN/N luciferase expression vector. The resulting DNA expression vector comprises the 3'UTR of the human VEGF protein gene containing the reported hypoxia domain inserted into the 3'UTR of the luciferase gene used in pGL2NeoN/N.

Example 15

Construction of a β-Galactosidase Hygromycin B Conferring Control Plasmid

In order to prepare the control plasmid, a pTK-Hyg plasmid (GenBank accession number: U40398), obtained from BD Biosciences, was modified to introduce unique restriction sites flanking the Hygromycin resistance conferring gene and regulatory elements. Since this Hygromycin cassette would be cloned into the SalI site of a second plasmid, pGL2-β-galactosidase, SalI and XhoI restriction sites were chosen to flank the HSV-TK promoter, Hyg$^r$ gene and HSV fragment containing TK polyA signal. Two primers, TKSF and TKSR were annealed and ligated into PflMI linearized pTK-Hyg (PflMI sites located at 2879 and 2928).

TKSF: 5'CTTGTCGACGATTCCC, SEQ ID NO:24, contains the SalI recognition site, identified in bold.

TKSR: 5'AATCGTCGACAAGTTC, SEQ ID NO:25, contains the SalI recognition site, identified in bold.

The resulting pTK-Hyg-SalI plasmid, was linearized with HindIII and dephosphorylated with calf intestinal phosphatase (CIP). Two primers, TKXF3 (5'-phos-AGCT-GCTAGCTCGAGATCTG) (SEQ ID NO: 26) and TKXR3 (5'-phos-AGCTCAGATCTCGAGCTAGC) (SEQ ID NO: 27) were annealed and ligated into HindIII linearized pTK-Hyg/SalI (HindIII site located at 1037 of original pTK-Hyg vector). The resulting plasmid was identified as pTK-Hyg-SalI/XhoI.

TKXF3: 5'-phos-AGCTGCTAGCTCGAGATCTG, SEQ ID NO:26, contains the XhoI recognition site, identified in bold.

TKXR3: 5'-phos-AGCTCAGATCTCGAGCTAGC, SEQ ID NO:27, contains the XhoI recognition site, identified in bold.

In order to prepare the pGL2-β-galactosidase plasmid (see FIG. 3B), a β-galactosidase conferring cassette (~3731 bp), obtained from a HindIII/BamHI restriction digest of pSV-β-Galactosidase Vector (Promega), was cloned into the CIP-treated, ~3104 bp HindIII/BamHI DNA fragment from pGL2-Control Vector (Promega) which contains the backbone plasmid and Amp$^r$, fl ori and SV40 Promoter sequences.

Figure 17:
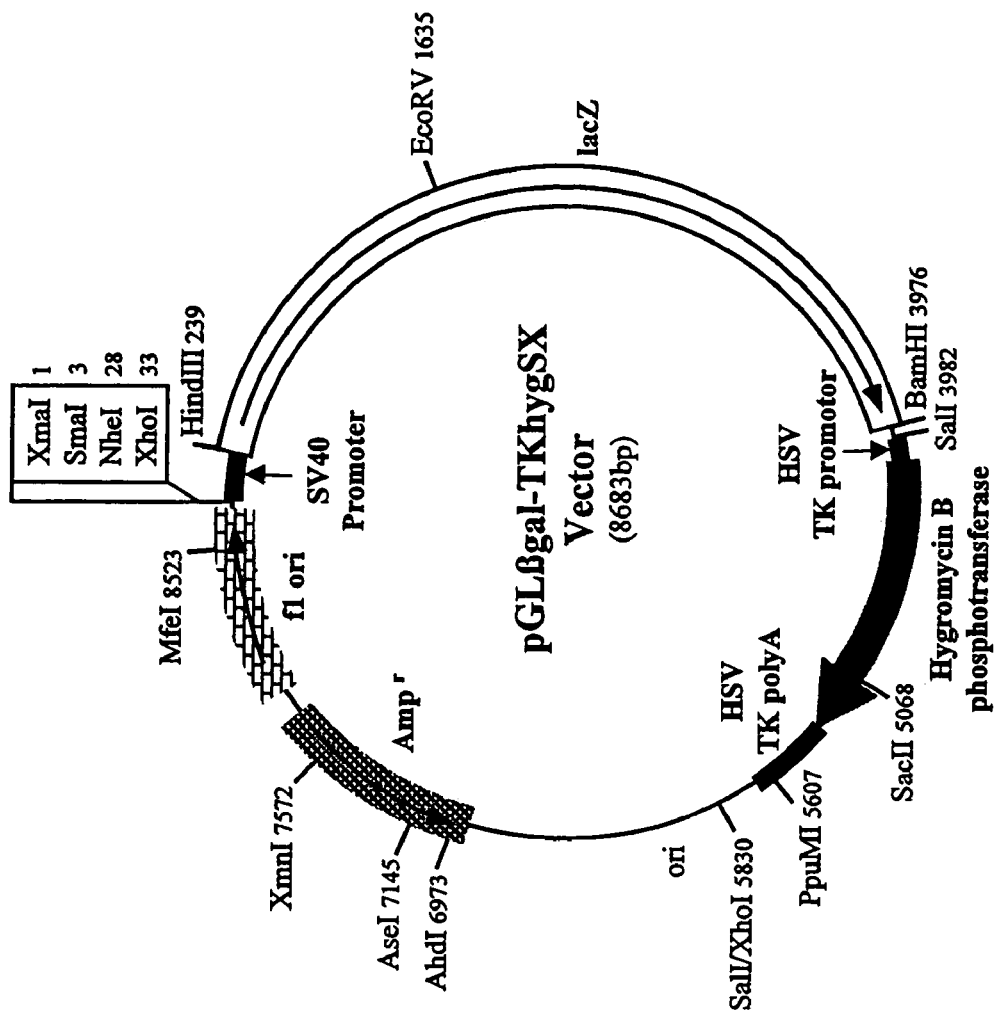
FIG. 17 shows the control plasmid, pGLβgal-TKhygSX.

The pTK-Hyg-SalI/XhoI plasmid was linearized with SalI and XhoI. The ~1840 bp SalI/XhoI fragment containing the Hygromycin conferring cassette, was ligated into SalI linearized and dephosphorylated pGL2-β-galactosidase plasmid. The resulting control plasmid (FIG. 17), identified as pGLβ-gal-TKhygSX (8683 bp), was verified by restriction digest and DNA sequencing.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

The embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A stably transfected cell line comprising: i) a DNA expression vector comprising a first DNA sequence encoding a first protein having a detectable signal, one or more 3' UTR sequence and one or more expression control sequence operatively associated with said first DNA sequence, and a heterologous instability sequence DNA that is heterologous to the 3'UTR sequence and inserted into the 3'UTR sequence, said instability sequence DNA comprising a second DNA sequence corresponding to one or more mRNA instability sequence which is from one or more naturally occurring gene sequences; and ii) a control DNA expression vector comprising a control DNA sequence encoding a second protein having a detectable signal, and one or more 3' UTR sequence and one or more expression control sequence operatively associated with said control DNA sequence, wherein said cell line is used for screening compounds which affect mRNA stability, wherein said heterologous instability sequence DNA is from about 200 to about 1500 nucleotides in length and comprises DNA corresponding to sequences that flank said mRNA instability sequence in the naturally occurring gene.

2. An assay system for screening for compounds which affect mRNA stability comprising a stably transfected cell line according to claim 1 and a test compound.

3. A stably transfected cell line according to claim 1, wherein said heterologous instability sequence DNA comprises DNA corresponding to the whole, or a substantial part, of the 3' UTR from said naturally occurring genes.

4. A stably transfected cell line according to claim 1, wherein said heterologous sequence DNA comprises DNA corresponding to one or more CRD from the coding region of said naturally occurring genes.

5. A stably transfected cell line according to claim 1, wherein said one or more naturally occurring genes is selected from the group consisting of a gene encoding a cytokine, a gene encoding a chemokine, a gene encoding a nuclear transcription factor, a gene encoding an oxygenase, a proto-oncogene, an immediate early gene, a cell cycle controlling gene, and a gene involved in apoptosis.

6. A set of stably transfected cell lines comprising: (i) a stably transfected cell line comprising a DNA expression vector comprising a first DNA sequence encoding a first protein having a detectable signal, one or more 3' UTR sequence and one or more expression control sequence operatively associated with said first DNA sequence, and a heterologous instability sequence DNA that is heterologous to the 3'UTR sequence and inserted into the 3'UTR sequence, said instability sequence DNA comprising a second DNA sequence corresponding to one or more mRNA instability sequence which is from one or more naturally occurring gene sequences; and (ii) a stably transfected cell line comprising a control DNA expression vector comprising a control DNA sequence encoding a second protein having a detectable signal, and one or more 3' UTR sequence and one or more expression control sequence operatively associated with said control DNA sequence, wherein said set of cell lines is used for screening compounds which affect mRNA stability, wherein said heterologous instability sequence DNA is from about 200 to about 1500 nucleotides in length and comprises DNA corresponding to sequences that flank said mRNA instability sequence in the naturally occurring gene.

7. A set of stably transfected cell lines according to claim 6, wherein said first and second proteins are the same protein.

8. A set of stably transfected cell lines according to claim 6, wherein said heterologous instability sequence DNA in the stably transfected cell line of (i) comprises DNA corresponding to the whole, or a substantial part, of the 3' UTR from said naturally occurring genes.

9. A set of stably transfected cell lines according to claim 6, wherein said heterologous instability sequence DNA in the stably transfected cell line of (i) comprises DNA corresponding one or more CRD from the coding region of said naturally occurring genes.

10. A set of stably transfected cell lines according to claim 6, wherein said one or more naturally occurring genes from which said second DNA sequence corresponding to one or more mRNA instability sequence in the stably transfected cell line of (i) is selected from the group consisting of a gene encoding a cytokine, a gene encoding a chemokine, a gene encoding a nuclear transcription factor, a gene encoding an oxygenase, a proto-oncogene, an immediate early gene, a cell cycle controlling gene, and a gene involved in apoptosis.

11. An assay system for screening for compounds which affect mRNA stability, comprising a set of stably transfected cell lines according to claim 6 and a test compound.

12. A stably transfected cell line according to claim 1, wherein the cell line is of the native cell type in which said mRNA instability sequence is produced.

13. A stably transfected cell line according to claim 1, wherein said cell line is used for high throughput screening of compounds which affect mRNA stability.

14. A stably transfected cell line according to claim 1, wherein said detectable signal is produced directly.

15. A stably transfected cell line according to claim 1, wherein said mRNA instability sequence is from the gene coding for IL-1β.

16. A stably transfected cell line according to claim 1, wherein said mRNA instability sequence is from the gene coding for APP.

17. A stably transfected cell line according to claim 1, wherein said mRNA instability sequence is from the gene coding for bcl-2α.

18. A stably transfected cell line according to claim 1, wherein said mRNA instability sequence is from the gene coding for c-myc.

19. A stably transfected cell line according to claim 1, wherein said mRNA instability sequence is from the gene coding for TNF-α.

20. A stably transfected cell line according to claim 1, wherein said mRNA instability sequence is from the gene coding for VEGF.

21. A stably transfected cell line according to claim 1, wherein said mRNA instability sequence contains two or more ARE.

* * * * *

UNITED STATES PATENT AND TRADEMARK OFFICE
CERTIFICATE OF CORRECTION

| | | |
|---|---|---|
| PATENT NO. | : 7,598,079 B2 | Page 1 of 1 |
| APPLICATION NO. | : 10/814634 | |
| DATED | : October 6, 2009 | |
| INVENTOR(S) | : Kastelic et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 594 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 30

<210> SEQ ID NO 1
<211> LENGTH: 1105
<212> TYPE: DNA
<213> ORGANISM: Homo Sapiens

<400> SEQUENCE: 1

| | | | | | |
|---|---|---|---|---|---|
| gcggccgcca | cagcagcctc | tgaagttgga | cagcaaaacc | attgcttcac | tacccatcgg | 60 |
| tgtccattta | tagaataatg | tgggaagaaa | caaacccgtt | ttatgattta | ctcattatcg | 120 |
| ccttttgaca | gctgtgctgt | aacacaagta | gatgcctgaa | cttgaattaa | tccacacatc | 180 |
| agtaatgtat | tctatctctc | tttacatttt | ggtctctata | ctacattatt | aatgggtttt | 240 |
| gtgtactgta | aagaatttag | ctgtatcaaa | ctagtgcatg | aatagattct | ctcctgatta | 300 |
| tttatcacat | agccccttag | ccagttgtat | attattcttg | tggtttgtga | cccaattaag | 360 |
| tcctacttta | catatgcttt | aagaatcgat | ggggatgct | tcatgtgaac | gtgggagttc | 420 |
| agctgcttct | cttgcctaag | tattccttc | ctgatcacta | tgcattttaa | agttaaacat | 480 |
| ttttaagtat | ttcagatgct | ttagagagat | ttttttttcc | atgactgcat | tttactgtac | 540 |
| agattgctgc | ttctgctata | tttgtgatat | aggaattaag | aggatacaca | cgtttgtttc | 600 |
| ttcgtgcctg | ttttatgtgc | acacattagg | cattgagact | tcaagctttt | cttttttgt | 660 |
| ccacgtatct | tgggtctttt | gataaagaaa | agaatccctg | ttcattgtaa | gcacttttac | 720 |
| ggggcgggtg | gggaggggtg | ctctgctggt | cttcaattac | caagaattct | ccaaaacaat | 780 |
| tttctgcagg | atgattgtac | agaatcattg | cttatgacat | gatcgctttc | tacactgtat | 840 |
| tacataaata | aattaaataa | aataaccccg | ggcaagactt | ttctttgaag | gatgactaca | 900 |
| gacattaaat | aatcgaagta | attttgggtg | gggagaagag | gcagattcaa | ttttctttaa | 960 |
| ccagtctgaa | gtttcattta | tgatacaaaa | gaagatgaaa | atggaagtgg | caatataagg | 1020 |
| ggatgaggaa | ggcatgcctg | gacaaacccct | tcttttaaga | tgtgtcttca | atttgtataa | 1080 |
| aatggtgttt | tcatgtagcg | gccgc | | | | 1105 |

<210> SEQ ID NO 2
<211> LENGTH: 904
<212> TYPE: DNA
<213> ORGANISM: Homo Sapiens

<400> SEQUENCE: 2

| | | | | | |
|---|---|---|---|---|---|
| gcggccgctg | aagtcaacat | gcctgcccca | acaaatatg | caaaaggttc | actaaagcag | 60 |
| tagaaataat | atgcattgtc | agtgatgtac | catgaaacaa | agctgcaggc | tgtttaagaa | 120 |
| aaaataacac | acatataaac | atcacacaca | cagacagaca | cacacacaca | caacaattaa | 180 |
| cagtcttcag | gcaaaacgtc | gaatcagcta | tttactgcca | aagggaaata | tcatttattt | 240 |
| tttacattat | taagaaaaaa | agatttattt | atttaagaca | gtcccatcaa | aactcctgtc | 300 |
| tttgaaaatc | cgaccactaa | ttgccaagca | ccgcttcgtg | tggctccacc | tggatgttct | 360 |
| gtgcctgtaa | acatagattc | gctttccatg | ttgttggccg | gatcaccatc | tgaagagcag | 420 |
| acggatggaa | aaaggacctg | atcattgggg | aagctggctt | tctggctgct | ggaggctggg | 480 |
| gagaaggtgt | tcattcactt | gcatttcttt | gccctggggg | ctgtgatatt | aacagaggga | 540 |
| gggttcctgt | gggggaagt | ccatgcctcc | ctggcctgaa | gaagagactc | tttgcatatg | 600 |
| actcacatga | tgcatacctg | gtgggaggaa | aagagttggg | aacttcagat | ggacctagta | 660 |

```
cccactgaga tttccacgcc gaaggacagc gatgggaaaa atgcccttaa atcataggaa      720 agtattttt taagctacca attgtgccga gaaaagcatt ttagcaattt atacaatatc       780
atccagtacc ttaagccctg attgtgtata ttcatatatt ttggatacgc accccccaac     840
tcccaatact ggctctgtct gagtaagaaa cagaatcctc tggaacttga ggaagtgcgg     900
ccgc                                                                  904
```

<210> SEQ ID NO 3
<211> LENGTH: 710
<212> TYPE: DNA
<213> ORGANISM: Homo Sapiens

<400> SEQUENCE: 3

```
gcggccgctg aagtcaacat gcctgcccca acaaatatg caaaaggttc actaaagcag       60
tagaaataat atgcattgtc agtgatgtac catgaaacaa agctgcaggc tgtttaagaa     120
aaaataacac acatataaac atcacacaca cagacagaca cacacacaca caacaattaa    180
cagtcttcag gcaaaacgtc gaatcagcta tttactgcca aagggaaata tcatttattt    240
tttacattat taagaaaaaa agatttatt atttaagaca gtcccatcaa aactcctgtc      300
tttggaaatc cgaccactaa ttgccaagca ccgcttcgtg tggctccacc tggatgttct    360
gtgcctgtaa acatagattc gctttccatg ttgttggccg gatcaccatc tgaagagcag    420
acggatggaa aaaggacctg atcattgggg aagctggctt tctggctgct ggaggctggg    480
gagaaggtgt tcattcactt gcatttcttt gccctggggg ctgtgatatt aacagaggga    540
gggttcctgt gggggaagt ccatgcctcc ctggcctgaa aagagactc tttgcatatg      600 actcacatga tgcataccctg gtgggaggaa agagttggg aacttcagat ggacctagta    660
cccactgaga tttccacgcc gaaggacagc gatgggaaaa atgcggccgc                710
```

<210> SEQ ID NO 4
<211> LENGTH: 688
<212> TYPE: DNA
<213> ORGANISM: Homo Sapiens

<400> SEQUENCE: 4

```
gcggccgctc ggagcttttt tgccctgcgt gaccagatcc cggagttgga aacaatgaa       60 aaggcccca aggtagttat ccttaaaaaa gccacagcat acatcctgtc cgtccaagca     120
gaggagcaaa agctcatttc tgaagaggac ttgttgcgga aacgacgaga acagttgaaa    180
cacaaacttg aacagctacg gaactcttgt gcgtaaggaa aagtaaggaa aacgattcct    240
tctgacagaa atgtcctgag caatcaccta tgaacttgtt tcaaatgcat gatcaaatgc    300
aacctcacaa ccttggctga gtcttgagac tgaaagattt agccataatg taaactgcct    360
caaattggac tttgggcata aaagaacttt tttatgctta ccatctttt ttttcttta      420 acagatttgt atttaagaat tgttttaaa aaattttaag atttacacaa tgtttctctg     480
taaatattgc cattaaatgt aaataacttt aataaaacgt ttatagcagt tacacagaat    540
ttcaatccta gtatatagta cctagtatta taggtactat aaaccctaat tttttttatt    600
taagtacatt ttgcttttta aagttgattt ttttctattg ttttagaaaa aaataaaata    660
actggcaaat atatcattga gccatatg                                        688
```

<210> SEQ ID NO 5
<211> LENGTH: 806
<212> TYPE: DNA

<213> ORGANISM: Homo Sapiens

<400> SEQUENCE: 5

| | | | | | |
|---|---|---|---|---|---|
| gcggccgctg | aggaggacga | acatccaacc | ttcccaaacg | cctcccctgc | cccaatccct | 60 |
| ttattacccc | ctccttcaga | caccctcaac | ctcttctggc | tcaaaagag | aattgggggc | 120 |
| ttagggtcgg | aacccaagct | tagaacttta | agcaacaaga | ccaccacttc | gaaacctggg | 180 |
| attcaggaat | gtgtggcctg | cacagtgaag | tgctggcaac | cactaagaat | tcaaactggg | 240 |
| gcctccagaa | ctcactgggg | cctacagctt | tgatccctga | catctggaat | ctggagacca | 300 |
| gggagccttt | ggttctggcc | agaatgctgc | aggacttgag | aagacctcac | ctagaaattg | 360 |
| acacaagtgg | accttaggcc | ttcctctctc | cagatgtttc | cagacttcct | tgagacacgg | 420 |
| agcccagccc | tccccatgga | gccagctccc | tctatttatg | tttgcacttg | tgattattta | 480 |
| ttatttattt | attatttatt | tatttacaga | tgaatgtatt | tatttgggag | accggggtat | 540 |
| cctgggggac | ccaatgtagg | agctgccttg | gctcagacat | gttttccgtg | aaaacggagc | 600 |
| tgaacaatag | gctgttccca | tgtagccccc | tggcctctgt | gccttctttt | gattatgttt | 660 |
| tttaaaatat | ttatctgatt | aagttgtcta | aacaatgctg | atttggtgac | caactgtcac | 720 |
| tcattgctga | gcctctgctc | cccaggggag | ttgtgtctgt | aatcgcccta | ctattcagtg | 780 |
| gcgagaaata | aagtttgctt | catatg | | | 806 |

<210> SEQ ID NO 6
<211> LENGTH: 613
<212> TYPE: DNA
<213> ORGANISM: Homo Sapiens

<400> SEQUENCE: 6

| | | | | | |
|---|---|---|---|---|---|
| gcggccgcta | aagagagctg | tacccagaga | gtcctgtgct | gaatgtggac | tcaatcccta | 60 |
| gggctggcag | aaagggaaca | gaaaggtttt | tgagtacggc | tatagcctgg | actttcctgt | 120 |
| tgtctacacc | aatgcccaac | tgcctgcctt | agggtagtgc | taagaggatc | tcctgtccat | 180 |
| cagccaggac | agtcagctct | ctcctttcag | ggccaatccc | cagcccttt | gttgagccag | 240 |
| gcctctctca | cctctcctac | tcacttaaag | cccgcctgac | agaaaccacg | gccacatttg | 300 |
| gttctaagaa | accctctgtc | attcgctccc | acattctgat | gagcaaccgc | ttccctattt | 360 |
| atttatttat | ttgtttgttt | gttttattca | ttggtctaat | ttattcaaag | ggggcaagaa | 420 |
| gtagcagtgt | ctgtaaaaga | gcctagtttt | taatagctat | ggaatcaatt | caatttggac | 480 |
| tggtgtgctc | tctttaaatc | aagtccttta | attaagactg | aaaatatata | agctcagatt | 540 |
| atttaaatgg | gaatatttat | aaatgagcaa | atatcatact | gttcaatggt | tctgaaataa | 600 |
| acttcaccat | atg | | | | 613 |

<210> SEQ ID NO 7
<211> LENGTH: 1101
<212> TYPE: DNA
<213> ORGANISM: Homo Sapiens

<400> SEQUENCE: 7

| | | | | | |
|---|---|---|---|---|---|
| gcggccgcat | tgctgtgctt | tggggattcc | ctccacatgc | tgcacgcgca | tctcgccccc | 60 |
| agggggcactg | cctggaagat | tcaggagcct | gggcggcctt | cgcttactct | cacctgcttc | 120 |
| tgagttgccc | aggaggccac | tggcagatgt | cccggcgaag | agaagagaca | cattgttgga | 180 |
| agaagcagcc | catgacagct | ccccttcctg | ggactcgccc | tcatcctctt | cctgctcccc | 240 |
| ttcctggggt | gcagcctaaa | aggacctatg | tcctcacacc | attgaaacca | ctagttctgt | 300 |

```
cccccccagga gacctggttg tgtgtgtgtg agtggttgac cttcctccat ccctggtcc      360 ttcccttccc ttcccgaggc acagagagac agggcaggat ccacgtgccc attgtggagg      420
cagagaaaag agaaagtgtt ttatatacgg tacttattta atatcccttt ttaattagaa      480
attaaaacag ttaatttaat taaagagtag ggttttttt cagtattctt ggttaatatt      540
taatttcaac tatttatgag atgtatcttt tgctctctct tgctctctta tttgtaccgg      600
tttttgtata taaaattcat gtttccaatc tctctctccc tgatcggtga cagtcactag      660
cttatcttga acagatattt aattttgcta acactcagct ctgccctccc cgatcccctg      720
gctccccagc acacattcct ttgaaataag gtttcaatat acatctacat actatatata      780
tatatttggc aacttgtatt tgtgtgtata tatatatata tatgtttatg tatatatgtg      840
attctgataa aatagacatt gctattctgt tttttatatg taaaaacaaa acaagaaaaa      900
atagagaatt ctacatacta aatctctctc cttttttaat tttaatattt gttatcattt      960
atttattggt gctactgttt atccgtaata attgtgggga aaagatatta acatcacgtc     1020
tttgtctcta gtgcagtttt tcgagatatt ccgtagtaca tatttatttt taaacaacga     1080
caaagaaata cagaacatat g                                              1101

<210> SEQ ID NO 8
<211> LENGTH: 168
<212> TYPE: DNA
<213> ORGANISM: Homo Sapiens

<400> SEQUENCE: 8
gcggccgcat tcctgtagac acacccaccc acatacatac atttatatat atatatatta       60
tatatatata aaataaaata tctctatttt atatatataa aatatatata ttcttttttt      120
aaattaacag tgctaatgtt attggtgtct tcactggatg aacatatg                   168

<210> SEQ ID NO 9
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 9
ttgcggccgc tacatgaaaa caccatttta tac                                    33

<210> SEQ ID NO 10
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 10
tgcggccgcc acagcagcct ctgaagttgg                                        30

<210> SEQ ID NO 11
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 11
agcggccgca cttcctcaag ttccagagg                                         29
```

```
<210> SEQ ID NO 12
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 12
agcggccgct gaagtcaaca tgcctgcc                                       28

<210> SEQ ID NO 13
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 13
agcggccgca tttttcccat cgctgtcc                                       28

<210> SEQ ID NO 14
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 14
ccatatggct caatgatata tttgccag                                       28

<210> SEQ ID NO 15
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 15
agcggccgct cggagctttt ttgccctgcg tg                                  32

<210> SEQ ID NO 16
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 16
ccatatgaag caaactttat ttctcgcc                                       28

<210> SEQ ID NO 17
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 17
agcggccgct gaggaggacg aacatccaac c                                   31

<210> SEQ ID NO 18
<211> LENGTH: 27
<212> TYPE: DNA
<213> ORGANISM: Artificial Sequence
<220> FEATURE:
<223> OTHER INFORMATION: oligonucleotide primer
```

-continued

```
<400> SEQUENCE: 18
ccatatggtg aagtttattt cagaacc                                27

<210> SEQ ID NO 19
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 19
agcggccgct aaagagagct gtacccagag                             30

<210> SEQ ID NO 20
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 20
aacatatgtt ctgtatttct ttgtcgttgt tt                          32

<210> SEQ ID NO 21
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 21
tgcggccgca ttgctgtgct ttggggattc cc                          32

<210> SEQ ID NO 22
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 22
aacatatgtt catccagtga agacaccaat aac                         33

<210> SEQ ID NO 23
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 23
tgcggccgca ttcctgtaga cacacccacc c                           31

<210> SEQ ID NO 24
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 24
cttgtcgacg attccc                                            16

<210> SEQ ID NO 25
```

```
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 25
aatcgtcgac aagttc                                              16

<210> SEQ ID NO 26
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 26
agctgctagc tcgagatctg                                          20

<210> SEQ ID NO 27
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 27
agctcagatc tcgagctagc                                          20

<210> SEQ ID NO 28
<211> LENGTH: 601
<212> TYPE: DNA
<213> ORGANISM: Homo Sapiens

<400> SEQUENCE: 28
agagagctgt acccagagag tcctgtgctg aatgtggact caatccctag ggctggcaga    60
aagggaacag aaaggttttt gagtacggct atagcctgga cttcctgtt gtctacacca   120 atgcccaact gcctgcctta gggtagtgct aagaggatct cctgtccatc agccaggaca   180
gtcagctctc tcctttcagg gccaatcccc agccctttg ttgagccagg cctctctcac    240
ctctcctact cacttaaagc ccgcctgaca gaaaccacgg ccacatttgg ttctaagaaa   300
ccctctgtca ttcgctccca cattctgatg agcaaccgct tccctattta tttatttatt   360
tgtttgtttg ttttattcat tggtctaatt tattccaaagg gggcaagaag tagcagtgtc   420
tgtaaaagag cctagttttt aatagctatg gaatcaattc aatttggact ggtgtgctct   480
ctttaaatca gtcctttaa ttaagactga aaatatataa gctcagatta tttaaatggg    540
aatatttata aatgagcaaa tatcatactg ttcaatggtt ctgaaataaa cttctctgaa   600
g                                                                  601

<210> SEQ ID NO 29
<211> LENGTH: 40
<212> TYPE: DNA
<213> ORGANISM: Homo Sapiens

<400> SEQUENCE: 29
atggcttccc tatttatta tttatttgtt tgtccaacct                      40

<210> SEQ ID NO 30
<211> LENGTH: 40
<212> TYPE: DNA
```

```
<213> ORGANISM: Homo Sapiens

<400> SEQUENCE: 30
ggataccgaa gggataaata aataaataaa caaacaggtt                                40
```